United States Patent
Wolters et al.

(10) Patent No.: US 12,011,196 B2
(45) Date of Patent: *Jun. 18, 2024

(54) ADJUSTABLE SPINE DISTRACTION IMPLANT

(71) Applicant: Life Spine, Inc., Huntley, IL (US)

(72) Inventors: Madeline C. Wolters, Carol Stream, IL (US); Michael S. Butler, Fishers, IN (US)

(73) Assignee: Life Spine Inc., Huntley, IL (US)

( * ) Notice: Subject to any disclaimer, the term of this patent is extended or adjusted under 35 U.S.C. 154(b) by 120 days.

This patent is subject to a terminal disclaimer.

(21) Appl. No.: 17/102,754

(22) Filed: Nov. 24, 2020

(65) Prior Publication Data

US 2021/0077159 A1 Mar. 18, 2021

Related U.S. Application Data

(63) Continuation of application No. 16/181,041, filed on Nov. 5, 2018, now Pat. No. 10,856,914, which is a (Continued)

(51) Int. Cl.
*A61B 17/70* (2006.01)
*A61F 2/44* (2006.01)
*A61B 17/00* (2006.01)

(52) U.S. Cl.
CPC ...... *A61B 17/7068* (2013.01); *A61B 17/7055* (2013.01); *A61B 17/7065* (2013.01);
(Continued)

(58) Field of Classification Search
CPC ............ A61B 17/7068; A61B 17/7055; A61B 17/7065; A61B 17/7047; A61B 17/7064; A61F 2/4405
See application file for complete search history.

(56) References Cited

U.S. PATENT DOCUMENTS

| | | |
|---|---|---|
| 4,466,426 A | 8/1984 | Blackman |
| 4,636,217 A | 1/1987 | Ogilvie et al. |

(Continued)

FOREIGN PATENT DOCUMENTS

| | | |
|---|---|---|
| KR | 20050119791 | 12/2005 |
| WO | WO-2006/102485 | 9/2006 |

(Continued)

OTHER PUBLICATIONS

Bacfuse® Spinous Process Fusion Plate Surgical Technique, 2011, Pioneer Surgical, 12 pages.
(Continued)

*Primary Examiner* — Tracy L Kamikawa
(74) *Attorney, Agent, or Firm* — Foley & Lardner LLP

(57) ABSTRACT

An adjustable implant includes a body portion including a first end, a second end including a bull nose, and a sidewall extending from the first end to the second end, a hook coupled to the body portion, the hook including a first hook portion extending from the body portion in a first direction, and a second hook portion extending from the first hook portion in a second direction that is different from the first direction, a first wing coupled to the first end of the body portion, and a second wing coupled to the body portion such that the distance between the first wing and the second wing is adjustable by a user, wherein the first and second wings include inward facing surfaces configured to be positioned adjacent portions of bone of a patient.

18 Claims, 24 Drawing Sheets

Related U.S. Application Data continuation of application No. 15/090,257, filed on Apr. 4, 2016, now Pat. No. 10,117,682, which is a continuation of application No. 13/247,664, filed on Sep. 28, 2011, now Pat. No. 9,301,788.

(52) U.S. Cl.
CPC . *A61B 2017/00858* (2013.01); *A61B 17/7047* (2013.01); *A61B 17/7064* (2013.01); *A61F 2/4405* (2013.01)

(56) References Cited

U.S. PATENT DOCUMENTS

| | | | |
|---|---|---|---|
| 5,390,683 A | 2/1995 | Pisharodi | |
| 5,645,599 A | 7/1997 | Samani | |
| 5,658,335 A | 8/1997 | Allen | |
| 5,658,337 A | 8/1997 | Kohrs et al. | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,126,660 A * | 10/2000 | Dietz | A61B 17/025 606/90 |
| 6,126,689 A | 10/2000 | Brett | |
| 6,176,882 B1 | 1/2001 | Biedermann et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,375,682 B1 | 4/2002 | Fleischmann et al. | |
| 6,409,766 B1 | 6/2002 | Brett | |
| 6,451,019 B1 | 9/2002 | Zucherman et al. | |
| 6,491,724 B1 | 12/2002 | Ferree | |
| 6,494,883 B1 | 12/2002 | Ferree | |
| 6,537,320 B1 | 3/2003 | Michelson | |
| 6,648,917 B2 | 11/2003 | Gerbec et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,723,126 B1 | 4/2004 | Berry | |
| 6,773,460 B2 | 8/2004 | Jackson | |
| 6,796,983 B1 | 9/2004 | Zucherman et al. | |
| 6,902,566 B2 | 6/2005 | Zucherman et al. | |
| 6,953,477 B2 | 10/2005 | Berry | |
| 7,018,415 B1 | 3/2006 | McKay | |
| 7,048,736 B2 | 5/2006 | Robinson et al. | |
| 7,087,055 B2 | 8/2006 | Lim et al. | |
| 7,101,375 B2 | 9/2006 | Zucherman et al. | |
| 7,306,628 B2 | 12/2007 | Zucherman et al. | |
| 7,695,513 B2 | 4/2010 | Zucherman et al. | |
| 7,704,281 B2 * | 4/2010 | Pasquet | A61B 17/7055 623/17.13 |
| 7,727,280 B2 | 6/2010 | McLuen | |
| 7,731,751 B2 | 6/2010 | Butler et al. | |
| 7,749,252 B2 | 7/2010 | Zucherman et al. | |
| 8,048,117 B2 | 11/2011 | Zucherman et al. | |
| 8,097,019 B2 | 1/2012 | Mitchell et al. | |
| 8,187,332 B2 | 5/2012 | McLuen | |
| 8,231,656 B2 | 7/2012 | Lee et al. | |
| 8,241,330 B2 | 8/2012 | Lamborne et al. | |
| 8,287,569 B1 | 10/2012 | Powell | |
| 8,343,190 B1 | 1/2013 | Mueller et al. | |
| 8,382,801 B2 | 2/2013 | Lamborne et al. | |
| 8,409,286 B2 | 4/2013 | McKay | |
| 8,500,778 B2 | 8/2013 | Jackson et al. | |
| 8,574,300 B2 | 11/2013 | McManus et al. | |
| 8,597,360 B2 | 12/2013 | McLuen et al. | |
| 8,603,142 B2 | 12/2013 | Robinson | |
| 8,632,595 B2 | 1/2014 | Weiman | |
| 9,186,262 B2 | 11/2015 | McLuen et al. | |
| 9,358,123 B2 | 6/2016 | McLuen et al. | |
| 9,370,434 B2 | 6/2016 | Weiman | |
| 9,532,883 B2 | 1/2017 | McLuen et al. | |
| 9,907,673 B2 | 3/2018 | Weiman et al. | |
| 9,974,665 B2 | 5/2018 | McLuen et al. | |
| 10,016,283 B2 | 7/2018 | McLuen et al. | |
| 10,085,849 B2 | 10/2018 | Weiman et al. | |
| 10,092,422 B2 | 10/2018 | McLuen et al. | |
| 10,098,757 B2 | 10/2018 | Logan et al. | |
| 10,098,759 B2 | 10/2018 | Weiman | |
| 10,111,760 B2 | 10/2018 | Knapp et al. | |
| 10,117,682 B2 * | 11/2018 | Wolters | A61B 17/7065 |
| 10,159,583 B2 | 12/2018 | Dietzel et al. | |
| 10,213,321 B2 | 2/2019 | Knapp et al. | |
| 10,292,830 B2 | 5/2019 | McLuen et al. | |
| 10,420,654 B2 | 9/2019 | Logan et al. | |
| 10,478,311 B2 | 11/2019 | Miccio et al. | |
| 10,512,550 B2 | 12/2019 | Bechtel et al. | |
| 10,575,966 B2 | 3/2020 | Logan et al. | |
| 10,682,240 B2 | 6/2020 | McLuen et al. | |
| 10,709,574 B2 | 7/2020 | McLuen et al. | |
| 10,729,560 B2 | 8/2020 | Baker et al. | |
| 10,729,562 B2 | 8/2020 | Knapp et al. | |
| 10,736,754 B2 | 8/2020 | McLuen et al. | |
| 10,842,644 B2 | 11/2020 | Weiman et al. | |
| 10,856,914 B2 * | 12/2020 | Wolters | A61B 17/7055 |
| 10,925,752 B2 | 2/2021 | Weiman | |
| 2001/0012938 A1 | 8/2001 | Zucherman et al. | |
| 2002/0128716 A1 | 9/2002 | Cohen et al. | |
| 2003/0040746 A1 | 2/2003 | Mitchell et al. | |
| 2003/0216736 A1 | 11/2003 | Robison et al. | |
| 2003/0236520 A1 | 12/2003 | Lim et al. | |
| 2004/0153156 A1 | 8/2004 | Cohen et al. | |
| 2004/0167625 A1 | 8/2004 | Beyar et al. | |
| 2004/0172134 A1 | 9/2004 | Berry | |
| 2004/0193159 A1 | 9/2004 | Zucherman et al. | |
| 2005/0033437 A1 | 2/2005 | Bao et al. | |
| 2005/0049590 A1 | 3/2005 | Alleyne et al. | |
| 2005/0131536 A1 | 6/2005 | Eisermann et al. | |
| 2005/0143827 A1 | 6/2005 | Globerman et al. | |
| 2005/0165398 A1 | 7/2005 | Reiley | |
| 2005/0196420 A1 | 9/2005 | Zucherman et al. | |
| 2005/0222681 A1 | 10/2005 | Richley et al. | |
| 2005/0228391 A1 | 10/2005 | Levy et al. | |
| 2005/0261769 A1 | 11/2005 | Moskowitz et al. | |
| 2005/0278036 A1 | 12/2005 | Leonard et al. | |
| 2006/0004447 A1 | 1/2006 | Mastrorio et al. | |
| 2006/0036258 A1 | 2/2006 | Zucherman et al. | |
| 2006/0064166 A1 | 3/2006 | Zucherman et al. | |
| 2006/0084988 A1 | 4/2006 | Kim | |
| 2006/0089718 A1 | 4/2006 | Zucherman et al. | |
| 2006/0095136 A1 | 5/2006 | McLuen | |
| 2006/0149385 A1 | 7/2006 | McKay | |
| 2006/0189999 A1 | 8/2006 | Zwirkoski | |
| 2006/0235521 A1 | 10/2006 | Zucherman et al. | |
| 2006/0241601 A1 | 10/2006 | Trautwein et al. | |
| 2006/0241643 A1 | 10/2006 | Lim et al. | |
| 2006/0241770 A1 | 10/2006 | Rhoda et al. | |
| 2006/0264938 A1 | 11/2006 | Zucherman et al. | |
| 2007/0142915 A1 | 6/2007 | Altarac et al. | |
| 2007/0233098 A1 | 10/2007 | Mastrorio et al. | |
| 2007/0255415 A1 | 11/2007 | Edie et al. | |
| 2007/0270812 A1 | 11/2007 | Peckham | |
| 2008/0051906 A1 * | 2/2008 | Malandain | A61B 17/7065 606/151 |
| 2008/0108990 A1 | 5/2008 | Mitchell et al. | |
| 2008/0114455 A1 | 5/2008 | Lange et al. | |
| 2008/0114456 A1 | 5/2008 | Dewey et al. | |
| 2008/0140207 A1 | 6/2008 | Olmos et al. | |
| 2008/0161818 A1 | 7/2008 | Kloss et al. | |
| 2008/0177391 A1 | 7/2008 | Mitchell et al. | |
| 2008/0183211 A1 | 7/2008 | Lamborne et al. | |
| 2008/0256716 A1 | 10/2008 | Wahrmund et al. | |
| 2008/0312741 A1 * | 12/2008 | Lee | A61B 17/7068 606/90 |
| 2009/0018586 A1 * | 1/2009 | Butler | A61B 17/7052 606/251 |
| 2009/0018662 A1 * | 1/2009 | Pasquet | A61B 17/7067 623/17.11 |
| 2009/0062915 A1 | 3/2009 | Kohm et al. | |
| 2009/0216276 A1 * | 8/2009 | Pasquet | A61B 17/7055 623/17.11 |

(56) References Cited

U.S. PATENT DOCUMENTS

| | | | |
|---|---|---|---|
| 2009/0292314 A1* | 11/2009 | Mangione | A61B 17/7062 623/17.11 |
| 2010/0179595 A1* | 7/2010 | Jackson | A61B 17/7065 606/86 A |
| 2010/0204732 A1* | 8/2010 | Aschmann | A61B 17/7062 606/249 |
| 2010/0241167 A1* | 9/2010 | Taber | A61B 17/7061 606/249 |
| 2011/0022090 A1 | 1/2011 | Gordon et al. | |
| 2011/0066186 A1 | 3/2011 | Boyer et al. | |
| 2011/0144692 A1* | 6/2011 | Saladin | A61B 17/7067 606/249 |
| 2011/0166600 A1 | 7/2011 | Lamborne et al. | |
| 2011/0172709 A1 | 7/2011 | Lyons et al. | |
| 2011/0172711 A1 | 7/2011 | Kirschman | |
| 2011/0184468 A1 | 7/2011 | Metcalf et al. | |
| 2011/0224731 A1 | 9/2011 | Smisson et al. | |
| 2011/0313457 A1* | 12/2011 | Reglos | A61B 17/7068 606/279 |
| 2012/0016418 A1 | 1/2012 | Chin et al. | |
| 2012/0059474 A1 | 3/2012 | Weiman | |
| 2012/0109203 A1 | 5/2012 | Dryer et al. | |
| 2012/0143252 A1 | 6/2012 | Robinson | |
| 2012/0150231 A1* | 6/2012 | Alamin | A61B 17/7059 606/279 |
| 2012/0221051 A1 | 8/2012 | Robinson | |
| 2012/0253395 A1 | 10/2012 | Linares | |
| 2012/0265204 A1 | 10/2012 | Schmierer et al. | |
| 2012/0296378 A1 | 11/2012 | Lee et al. | |
| 2013/0079880 A1 | 3/2013 | Wolters et al. | |
| 2014/0194991 A1 | 7/2014 | Jimenez | |

FOREIGN PATENT DOCUMENTS

| | | |
|---|---|---|
| WO | WO-2006/105437 A2 | 10/2006 |
| WO | WO-2006/110578 A2 | 10/2006 |
| WO | WO-2007/121070 A2 | 10/2007 |
| WO | WO-2009/124269 A1 | 10/2009 |
| WO | WO-2011/019758 A2 | 2/2011 |

OTHER PUBLICATIONS

Communication and Search Report for European Application No. 12836814.9, dated Oct. 7, 2015, 10 pages.

International Search Report and Written Opinion for International Application No. PCT/US2012/057324, dated Dec. 20, 2012, 10 pages.

\* cited by examiner

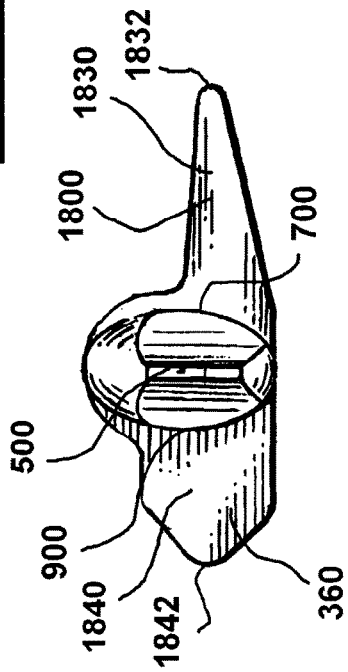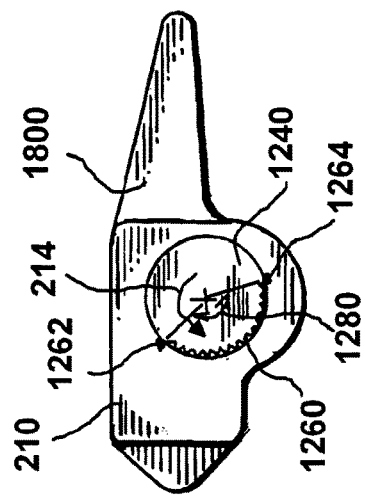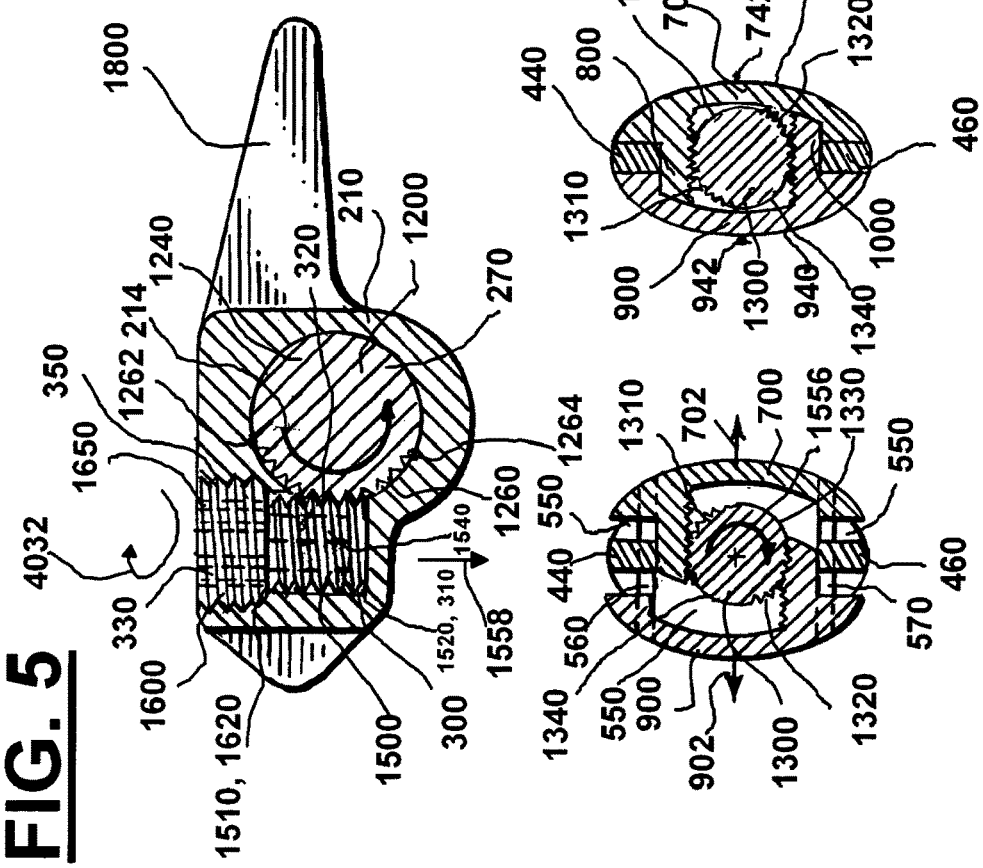

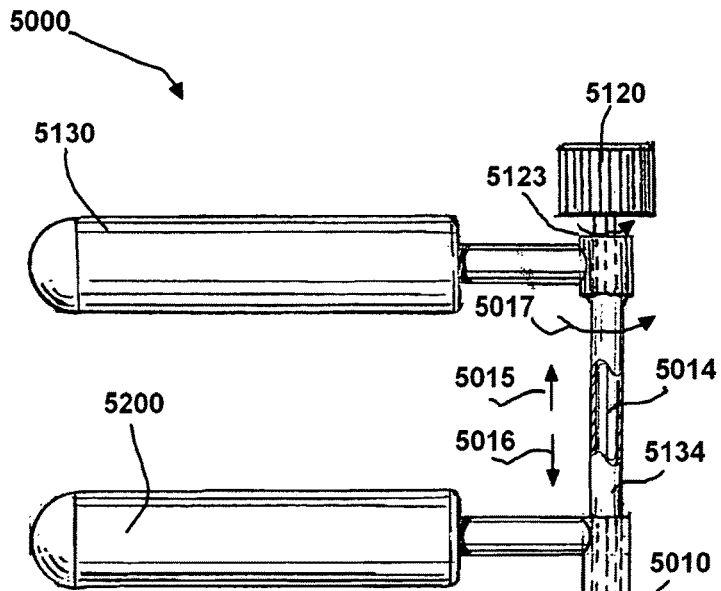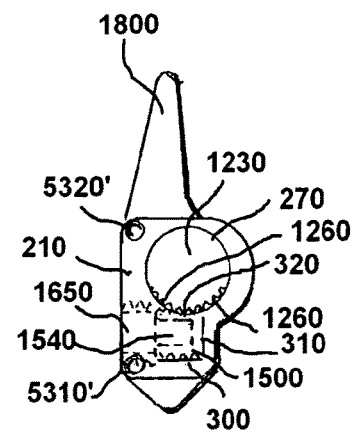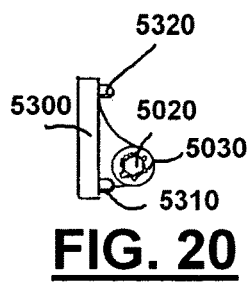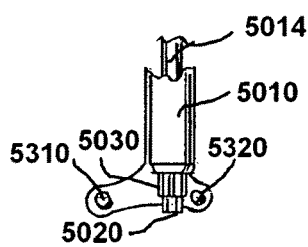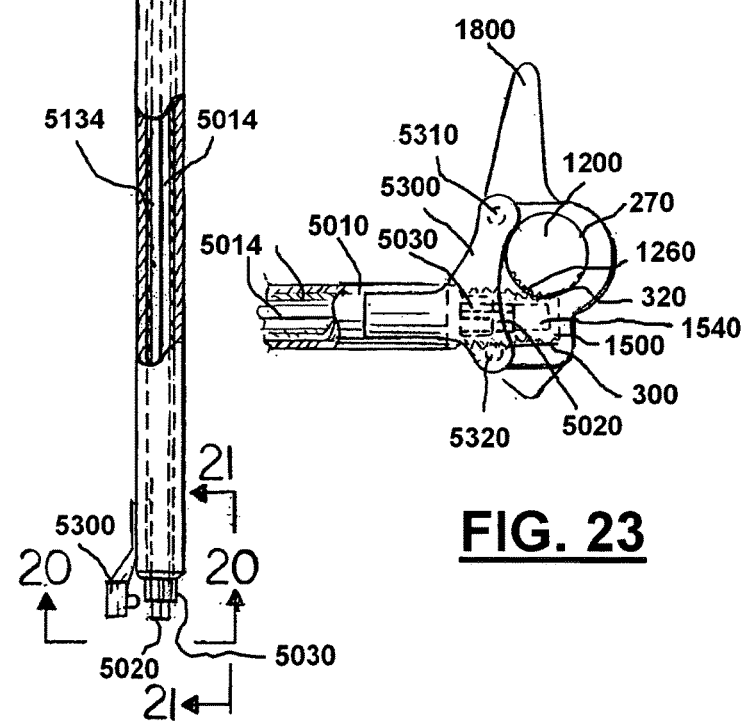

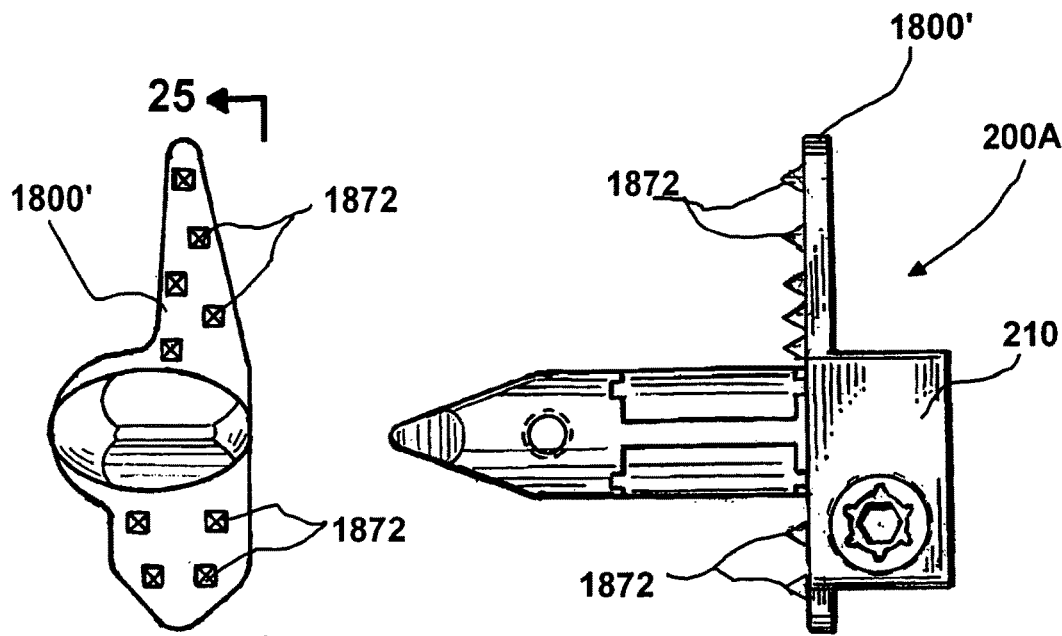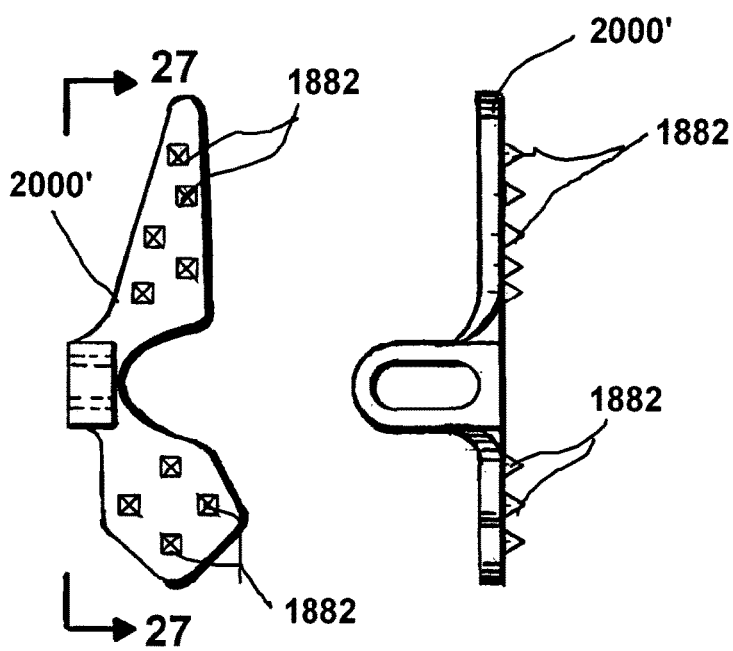
FIG. 24  FIG. 25  FIG. 26  FIG. 27

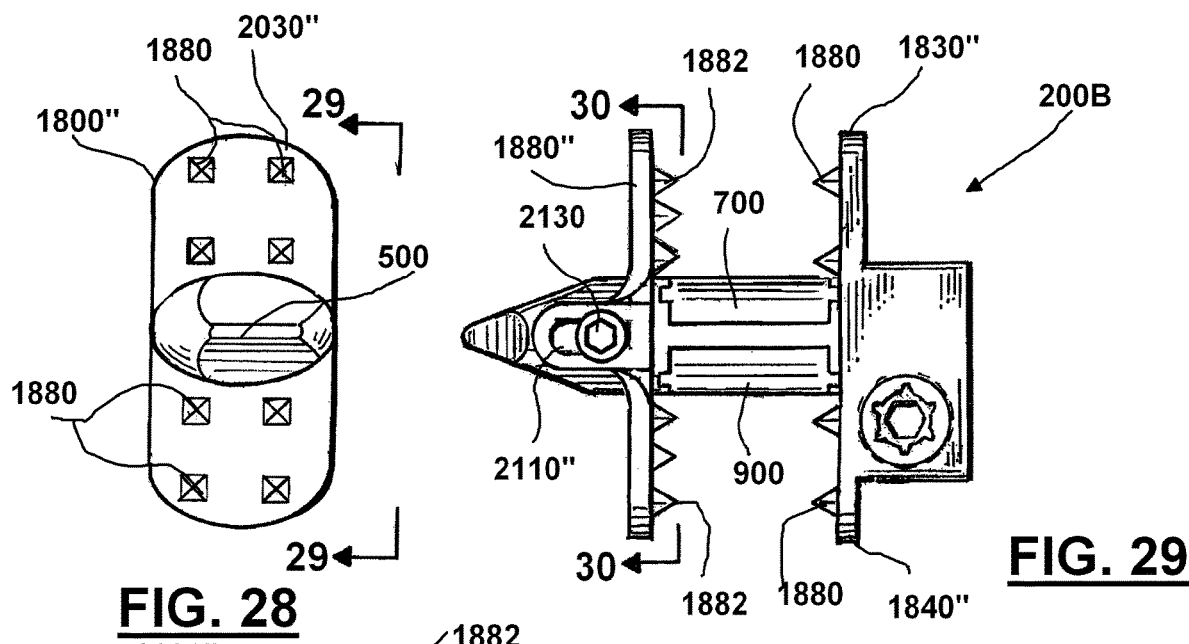
FIG. 28
FIG. 29
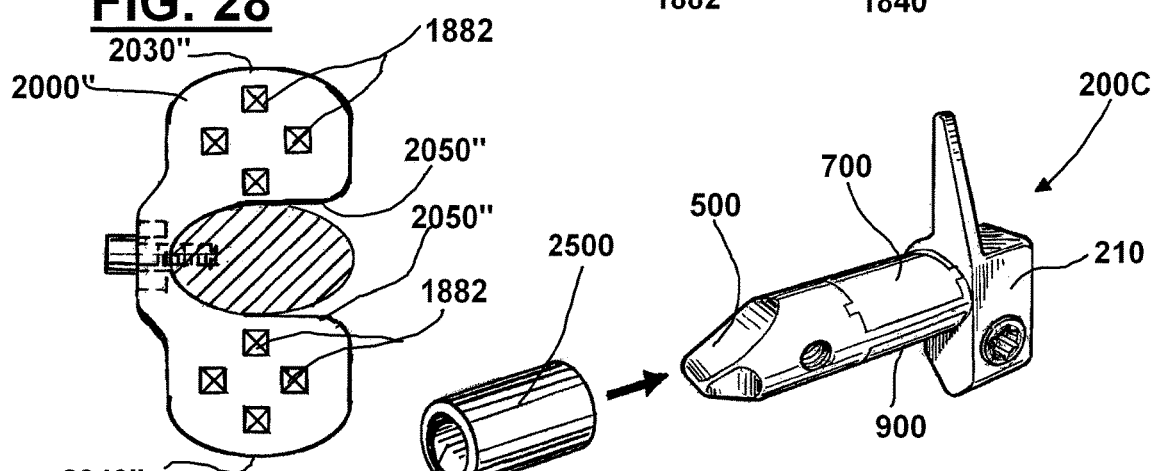
FIG. 30
FIG. 31
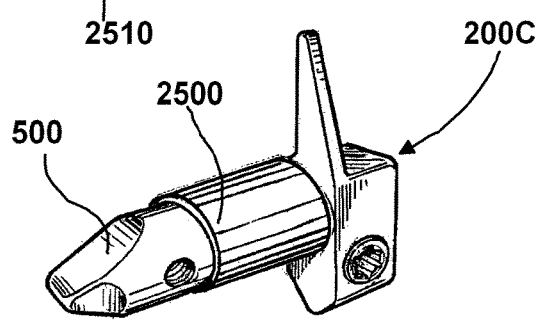
FIG. 32

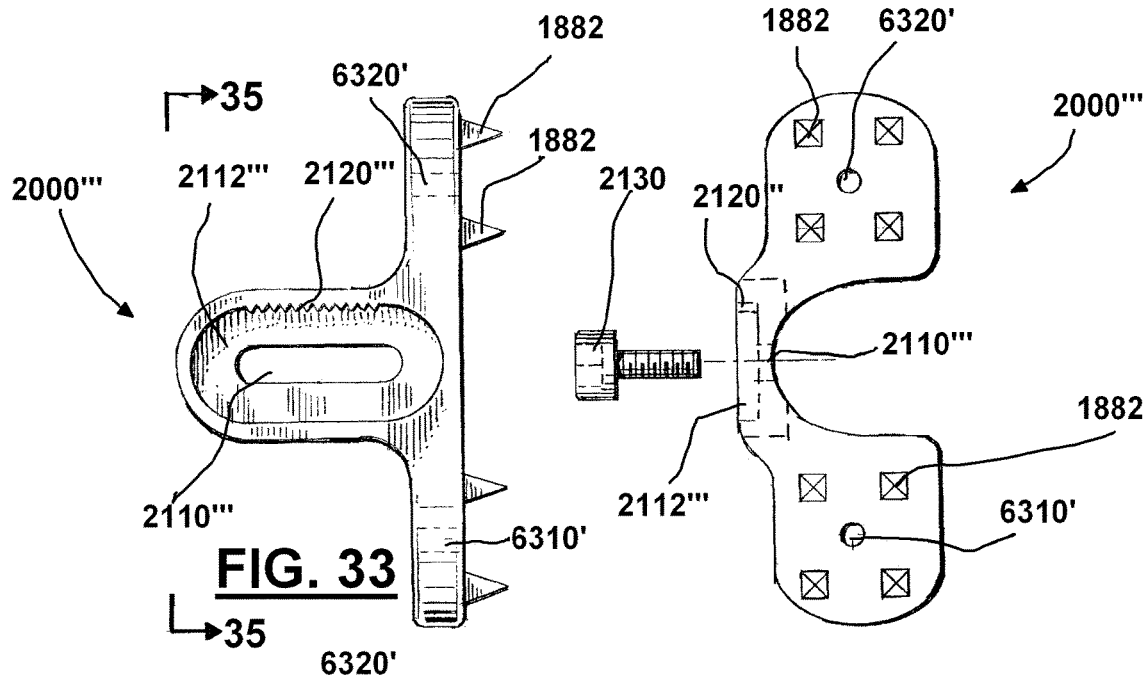
FIG. 33
FIG. 34
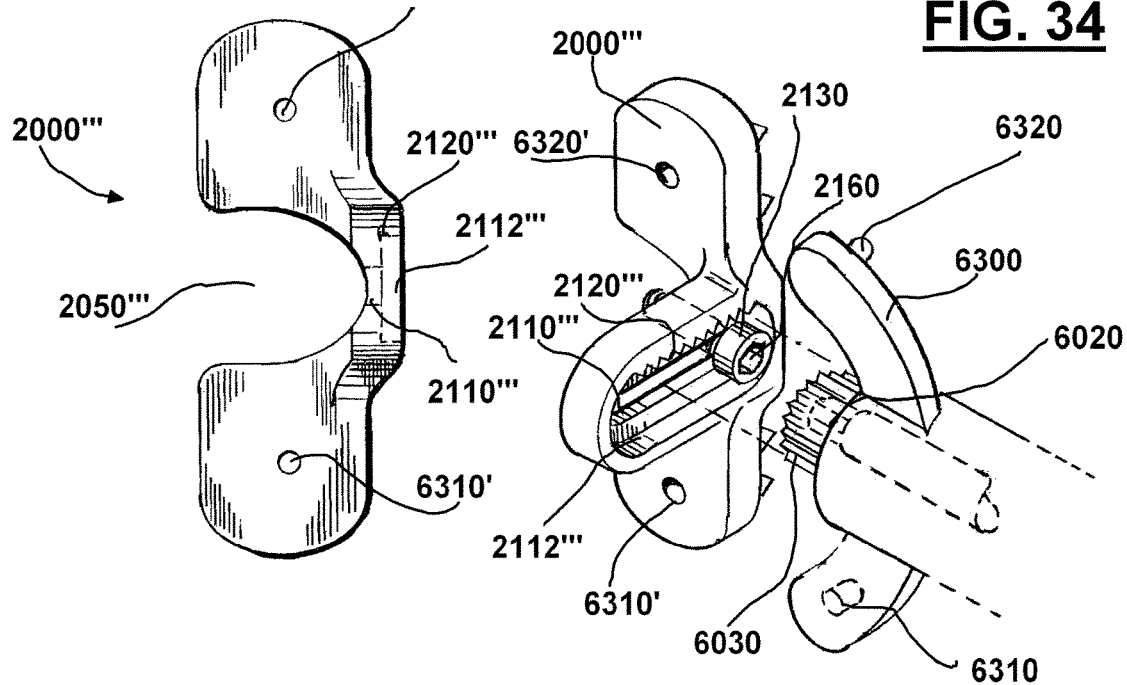
FIG. 35
FIG. 36

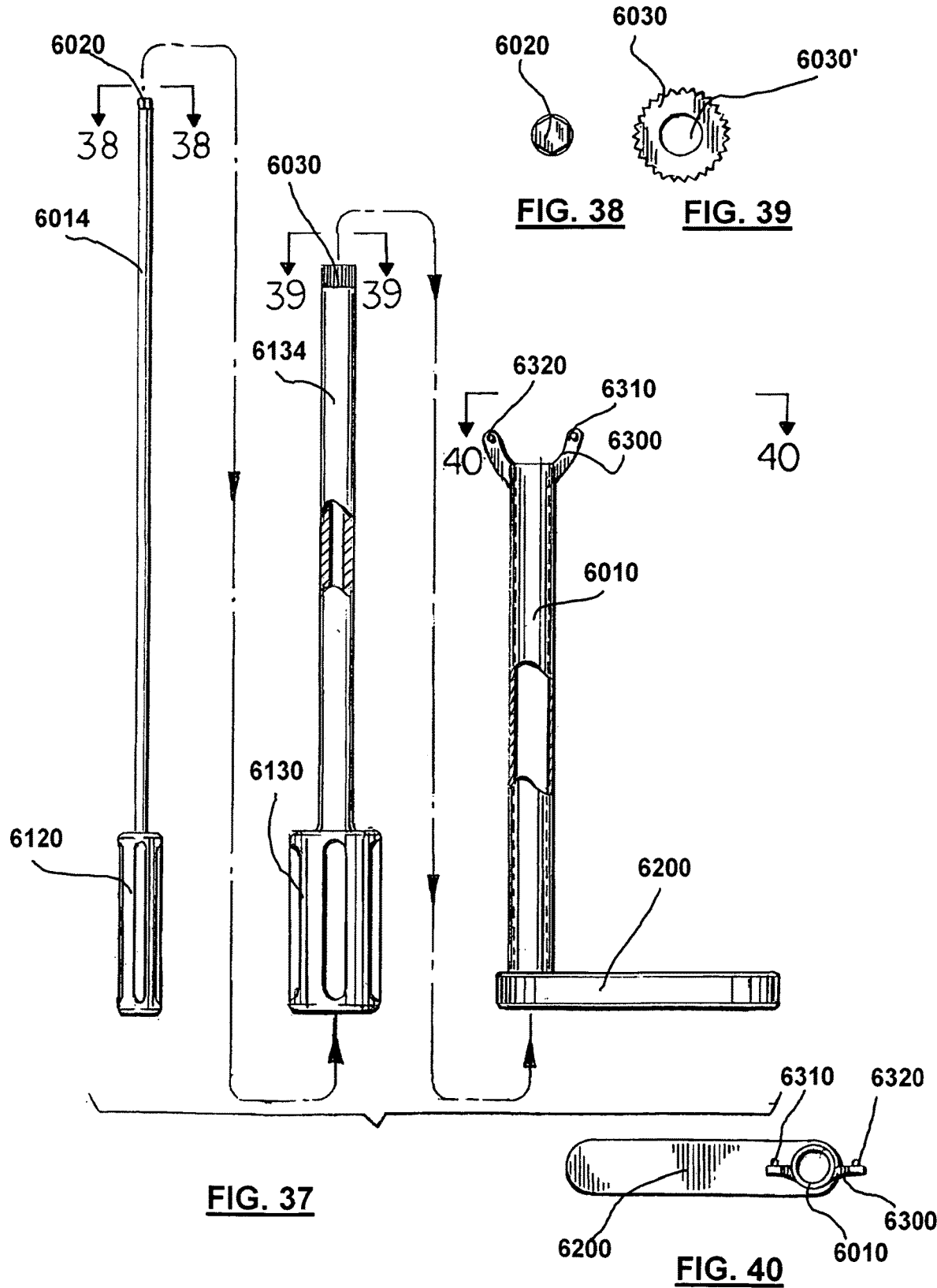

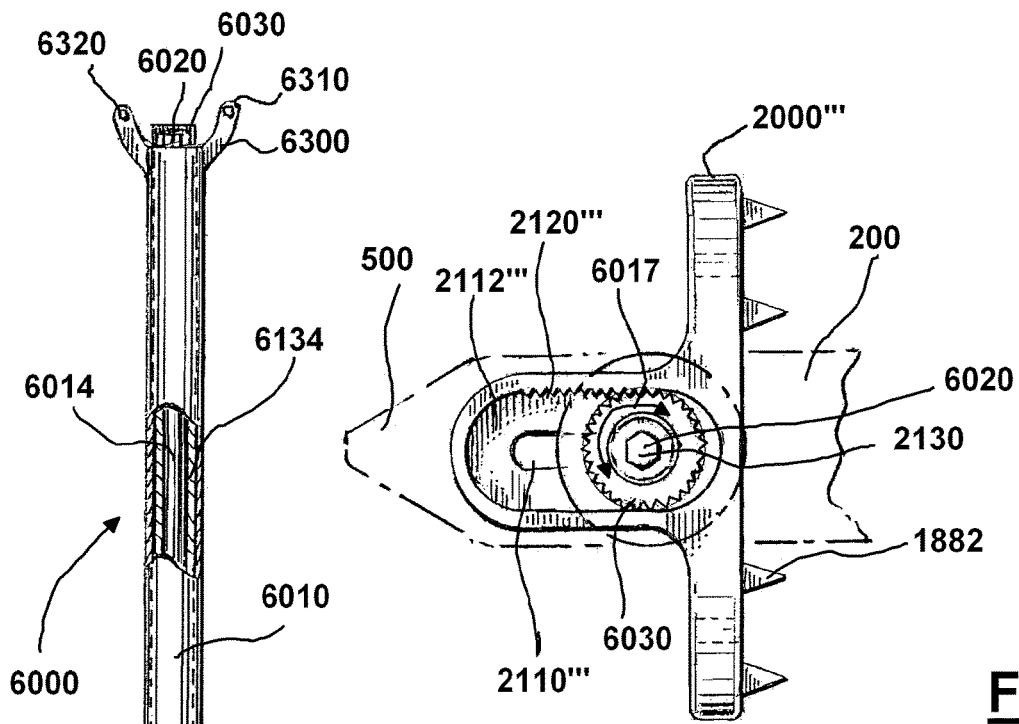
FIG. 42
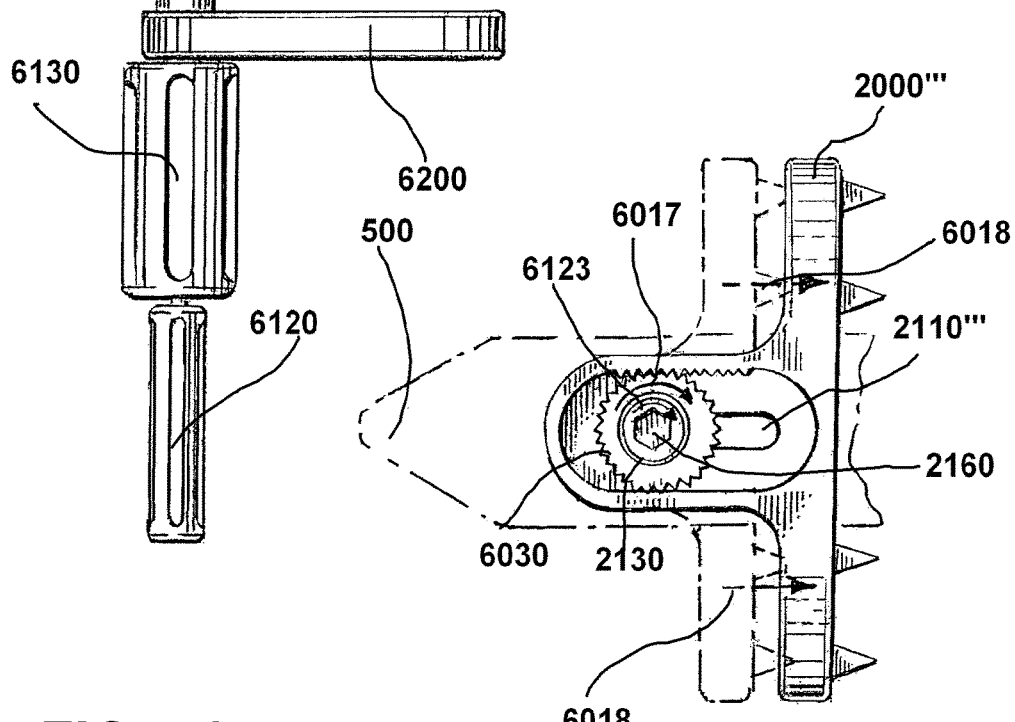
FIG. 41
FIG. 43

ADJUSTABLE SPINE DISTRACTION IMPLANT

CROSS-REFERENCE TO RELATED PATENT APPLICATIONS

This application is a continuation of U.S. application Ser. No. 16/181,041, filed on Nov. 5, 2018 (Issued as U.S. Pat. No. 10,856,914), which is a continuation of U.S. application Ser. No. 15/090,257 (Issued as U.S. Pat. No. 10,117,682), filed Apr. 4, 2016, which is a continuation of U.S. application Ser. No. 13/247,664 (Issued as U.S. Pat. No. 9,301,788), filed Sep. 28, 2011, which are incorporated herein by reference in their entireties.

BACKGROUND

The spine includes a row of 26 bones in the back and allows a person to stand up straight and bend over. The spine also protects a person's spinal cord from being injured. In people with spinal stenosis, the spine is narrowed in one or more of three parts: (1) the space at the center of the spine; (2) the canals where nerves branch out from the spine; and (3) the space between vertebrae (the bones of the spine). This narrowing puts pressure on the spinal cord and nerves and can cause pain.

Caused by aging spinal stenosis is most common in men and women over 50 years old. Younger people who were born with a narrow spinal canal or who hurt their spines may also get spinal stenosis. Changes that occur in the spine as people get older are the most common cause of spinal stenosis such as: (a) the bands of tissue that support the spine may get thick and hard; (b) bones and joints may get bigger; and (c) surfaces of the bones may bulge out, which are called bone spurs.

In some cases arthritis, a degenerative condition, can cause spinal stenosis. Two forms of arthritis that may affect the spine are: (a) osteoarthritis and (b) rheumatoid arthritis.

Osteoarthritis is the most common form of arthritis and most often occurs in middle-aged and older people. It may involve many joints in the body where it wears away the tough tissue (cartilage) that keeps the joints in place and can cause bone spurs and problems with joints.

Rheumatoid Arthritis affects most people at a younger age than osteoarthritis. It causes the soft tissues of the joints to swell and can affect internal organs and systems. However, it is not a common cause of spinal stenosis but can cause severe damage, especially to joints.

Some people are born with conditions that cause spinal stenosis. For instance, some people are born with a small spinal canal. Others are born with a curved spine (scoliosis). Other causes of spinal stenosis are: tumors of the spine; injuries; Paget's disease (a disease that affects the bones); too much fluoride in the body; and calcium deposits on the ligaments that run along the spine.

In many cases there may be no symptoms of spinal stenosis, or symptoms may appear slowly and get worse over time. Signs of spinal stenosis include: pain in the neck or back; numbness, weakness, cramping, or pain in the arms or legs; pain going down the leg; and foot problems.

One type of spinal stenosis, cauda equine syndrome, is very serious. This type occurs when there is pressure on nerves in the lower back. Symptoms may include: loss of control of the bowel or bladder; problems having sex; and pain, weakness, or loss of feeling in one or both legs.

Because spinal stenosis has many causes and symptoms, treatment may be required from doctors who specialize in certain aspects of the condition. Health care providers can include: rheumatologists (doctors who treat arthritis and related disorders); neurologists and neurosurgeons (doctors who treat diseases of the nervous system); orthopedic surgeons (doctors who treat problems with the bones, joints, and ligaments); and physical therapists.

As people age the amount of adverse spinal conditions tend to increase. For example, increases in spinal stenosis, such as central canal and lateral stenosis, along with the thickening Accordingly, it is desired to develop procedures and implants for surgically addressing stenosis through minimally invasive procedures, and preferably such surgical procedures can be performed on an outpatient basis.

U.S. Pat. No. 7,101,375 is incorporated herein by reference.

SUMMARY

One embodiment provides a minimally invasive adjustable implant and method for alleviating discomfort associated with the spinal column.

One embodiment provides a method and apparatus for relieving pain by relieving the pressure and restrictions on the blood vessels and nerves associated with the spine. This can be accomplished using an adjustable implant and method which distracts the spinous process of adjacent vertebra in order to alleviate the problems caused by spinal stenosis, facet arthropathy, and similar conditions.

One embodiment provides an adjustable implant for relieving pain comprising an adjustable device positioned between a first spinous process and a second spinous process. The adjustable device includes a vertebra expander or distractor.

One embodiment provides an adjustable implant which is positioned between a first spinous process and a second spinous process, and includes at least one expandable distraction wedge or plate that can adjustably distract the first and second spinous processes as the implant is positioned between the spinous processes as the wedging is expanded and/or retracted. In one embodiment two expandable wedging members are provided which can expand in substantially opposite directions.

One embodiment provides an adjustable implant adapted for increasing the volume and/or cross sectional area of the spinal canal and/or the neural foramen as the implant is positioned between adjacent spinous processes.

One embodiment provides a method for relieving pain due to conditions such as spinal stenosis and facet arthropathy. The method includes the steps of accessing adjacent first And second spinal processes of the spinal column and using an adjustable implant to distract these processes a sufficient amount in order to increase the volume and/or cross sectional area of the spinal canal and relieve pain.

One embodiment provides a method and apparatus which includes implanting an adjustable device which can be adjusted in order to achieve a desired amount of distraction and also maintain such distraction.

One embodiment provides an adjustable implant including a first portion and a second portion. The portions can be expanded and/or retracted in order to achieve the desired amount of distraction.

One embodiment provides an adjustable implant which includes an adjustable body. The adjustable central body can include first and second portions which can be expanded and/or retracted in order to achieve the desired amount of distraction.

One embodiment provides an adjustable implant which includes a first unit having an adjustable central body with a first wing at the first end of the unit. The adjustable implant can includes a guide extending from a second end of the unit and spaced apart from the first wing. The adjustable implant can further include a second wing which can be detachably connectable to the first unit, wherein the adjustable central body is located between the first and second wings.

One embodiment provides an adjustable implant with adjustable body having first and second wings, wherein at least one of the first and second wings is also adjustable relative to the other wing to accommodate spinous processes of different sizes.

One embodiment includes an implant with an adjustable body to be able to accommodate the anatomical structure of multiple spinous processes and different sizes of spinous processes.

One embodiment includes an adjustable implant with an adjustable body, the adjustable body having an elliptical cross section. In other embodiments the cross section can be circular, polygonal, square, rectangular, trapezoidal, quadrilateral, etc. In other embodiments the cross section can be symmetric. In other embodiments the cross section can non-symmetric, such as one shape of one side of the cross section and another shape on the other side of the cross section. For example, the cross section can have a half elliptical cross section on one side and a rectangular cross section on the other side. In other embodiments various permutations of the above specified shapes can be on each side of the cross section.

Another embodiment relates to an adjustable spinal implant comprising a body portion; a first wing coupled to a first end of the body portion; and a second wing adjustably coupled to the body portion such that the distance between the first wing and the second wing is adjustable by a user; wherein the first and second wings include inward facing surfaces configured to be positioned adjacent spinous processes of a patient, wherein each inward facing surface comprises a recess extending over a substantial portion of the inward facing surface.

Another embodiment relates to an adjustable spinal implant comprising a body portion comprising a pair of adjustable wedging members configured to interface with adjacent vertebral bodies; a first wing coupled to a first end of the body portion, the first wing comprising a first inward facing surface configured to be positioned adjacent a spinous process and at least one first projection configured to extend at least partially into the spinous process; a second wing coupled to the body portion, the second wing comprising a second inward facing surface configured to be positioned adjacent an opposite side of the spinous process from the first inward facing surface, the second wing further comprising at least one second projection configured to extend at least partially into the spinous process; wherein the body portion, the first wing, and the second wing each comprises at least one aperture extending there through and configured to receive a bone composite material configured to promote vertebral bone growth.

Another embodiment relates to an adjustable spinal implant comprising a body; a first wing coupled to the body; a second wing coupled to the body, the second wing being adjustable relative to the first wing along a length of the body; wherein each of the first wing and second wing comprises an extension extending from a central portion, the extension portion having a plurality of projections configure to engage a spinous process, the extension portion being adjustable relative to the central portion.

Various embodiments of the method and apparatus can be used to increase the volume and/or cross sectional area of the spinal canal thereby alleviating restrictions on vessels and nerves associated therewith, and reducing pain caused by such restrictions.

While certain novel features of this invention shown and described below are pointed out in the annexed claims, the invention is not intended to be limited to the details specified, since a person of ordinary skill in the relevant art will understand that various omissions, modifications, substitutions and/or changes in the forms and details of the device illustrated and in its operation may be made without departing in any way from the spirit of the present invention. No feature of the invention is critical or essential unless it is expressly stated as being "critical" or "essential."

BRIEF DESCRIPTION OF THE DRAWINGS

FIG. 3 is an end view of the body portion, taken along lines 3-3 of FIG. 1;

FIG. 4 is an end view of the body portion, taken along lines 4-4 of FIG. 1;

FIG. 5 is a sectional view of the body portion taken along the lines 5-5 of FIG. 1;

FIG. 6 is a sectional view of the body portion taken along the lines 6-6 of FIG. 1;

FIG. 7 is a partial sectional view of the body portion in an expanded position;

FIG. 19 is an elevation view of an adjusting tool;

FIG. 20 is a fragmentary view of the adjusting tool taken along lines 20-20 of FIG. 19;

FIG. 21 is a fragmentary view of the adjusting tool taken along lines 21-21 of FIG. 19;

FIG. 22 is a side view of the body;

FIG. 23 is a side view of the body with adjusting tool engaged;

FIG. 24 is an end view of a second embodiment of the apparatus of the present invention;

FIG. 25 is a side taken along lines 25-25 of FIG. 24;

FIG. 26 is a side view of a fixture or wing part of the second embodiment of the apparatus of the present invention;

FIG. 27 is a side view taken along lines 27-27 of FIG. 26;

FIG. 28 is a side view of a third embodiment of the apparatus of the present invention;

FIG. 29 is a view taken along lines 29-29 of FIG. 28;

FIG. 30 is a view taken along lines 30-30 of FIG. 29;

FIG. 31 is a perspective view of a fourth embodiment of the apparatus of the present invention; and FIG. 32 is a perspective view of a fourth embodiment of the apparatus of the present invention.

FIG. 33 is a top view of an alternative embodiment of a second wing which is laterally adjustable relative to the first wing.

FIG. 34 is a side view of the wing of FIG. 33.

FIG. 35 is a side view of the wing of FIG. 33 taken from the lines 35-35.

FIG. 36 is a perspective view showing wing adjustment tool being connected to the Second wing of FIG. 33.

FIG. 37 is a side view showing the three pieces of wing adjustment tool.

FIG. 38 is a bottom view of the wing adjustment tool taken from the lines 38-38 of FIG. 37.

FIG. 39 is a bottom view of the wing adjustment tool taken from the lines 39-39 of FIG. 37.

FIG. 40 is a top view of the wing adjustment tool of FIG. 37.

FIG. 41 is a partial sectional view of the wing adjustment tool of FIG. 37.

FIG. 42 is a top view of the wing adjustment tool of FIG. 37 connected to the second wing of FIG. 33.

FIG. 43 shows the second wing being laterally adjusted.

DETAILED DESCRIPTION

Figure 16:
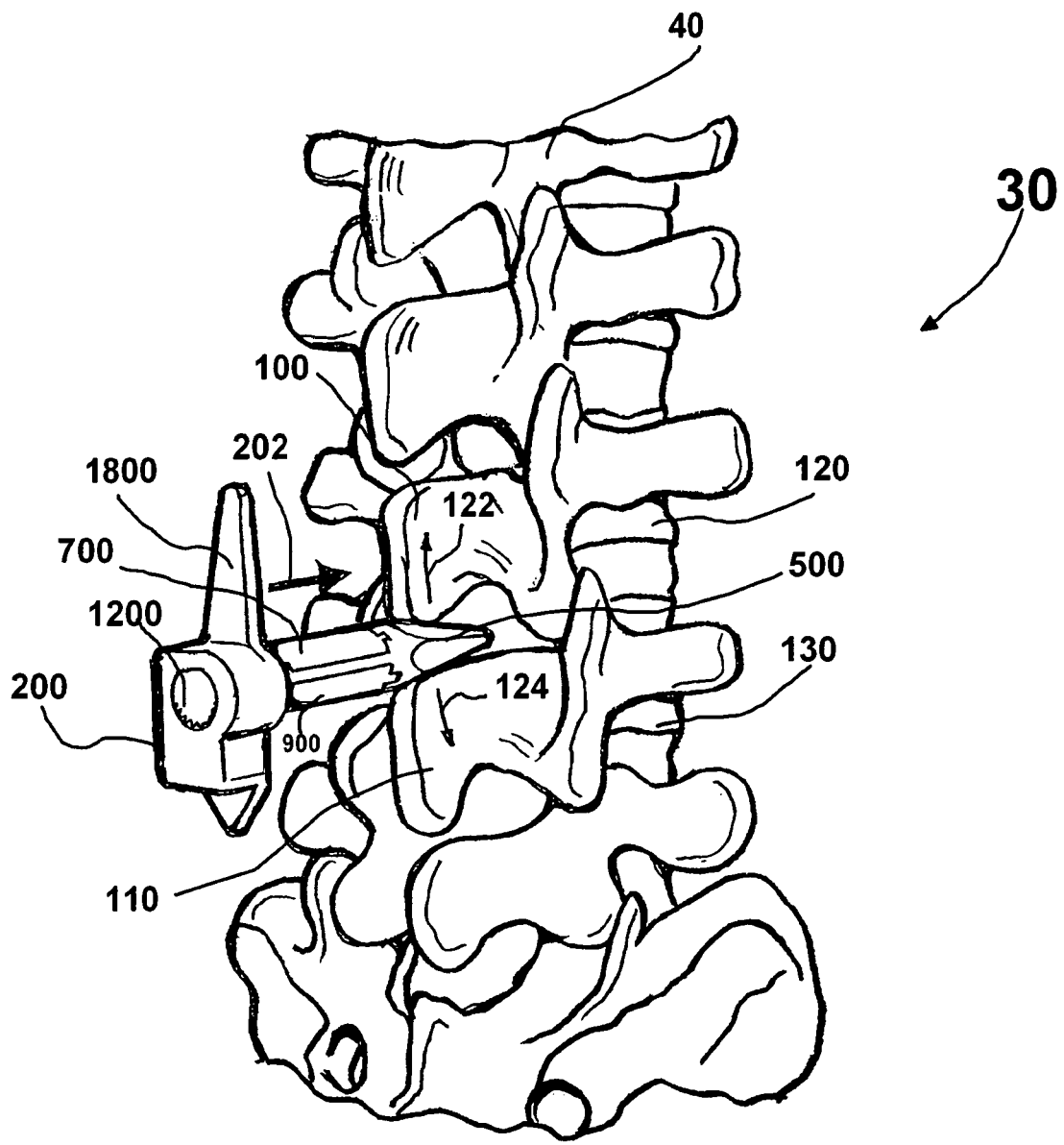
FIG. 16 is a perspective, partially exploded view of the preferred embodiment of the apparatus of the present invention illustrating implantation.
Figure 17:
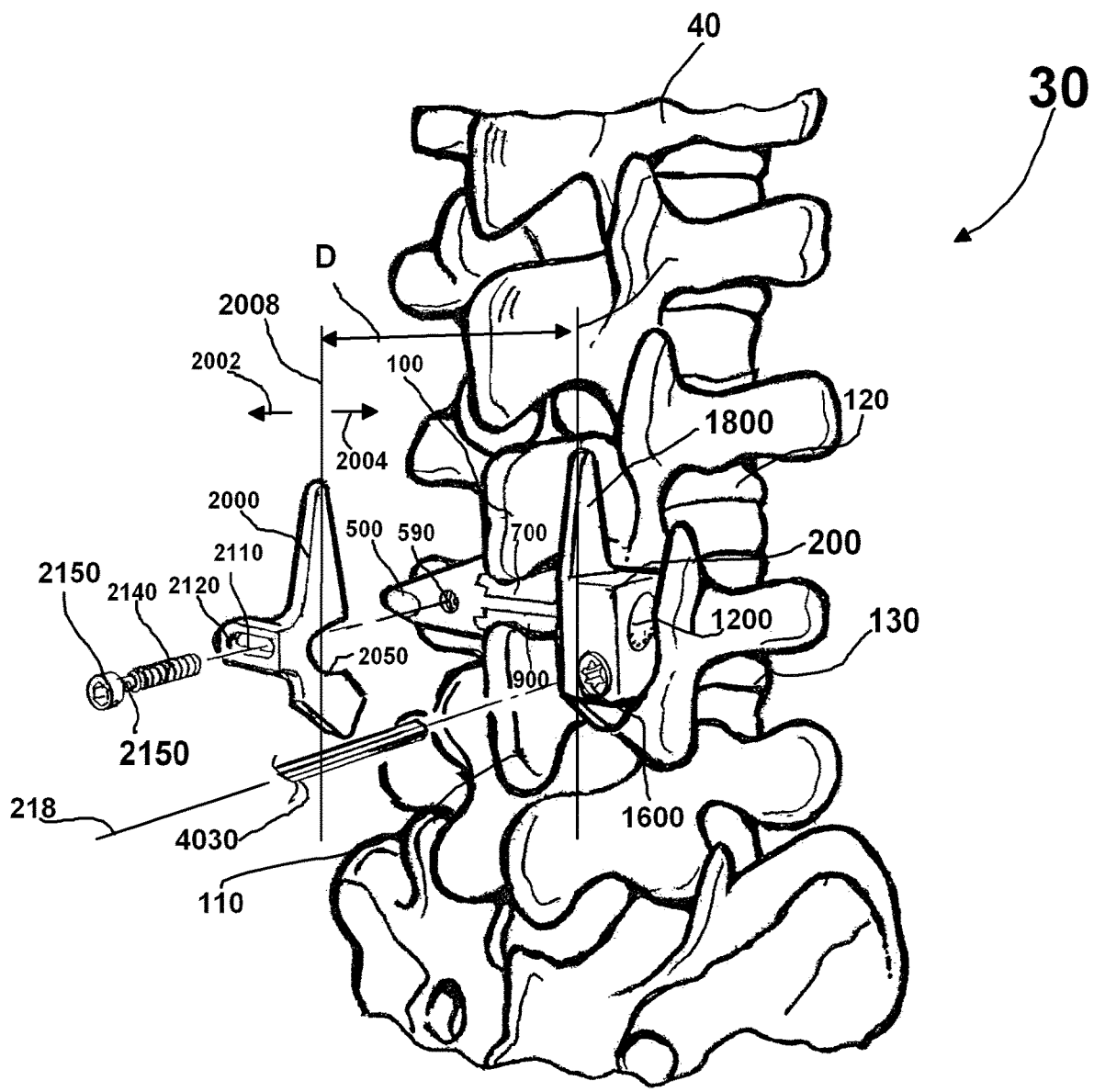
FIG. 17 is a perspective view of the preferred embodiment of the apparatus of the present invention illustrating implantation.
Figure 18:
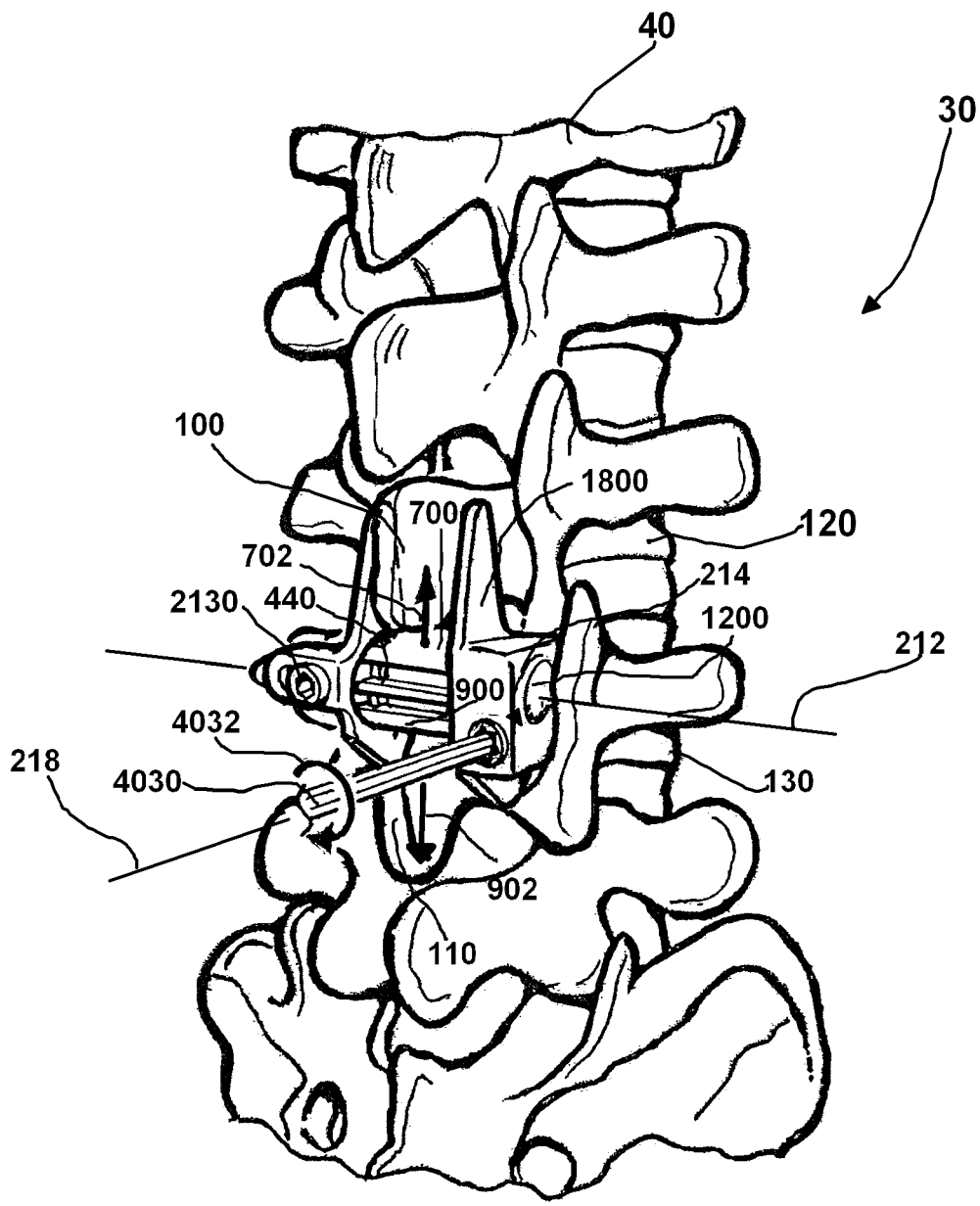
FIG. 18 is a perspective view of the preferred embodiment of the apparatus of the present invention illustrating implantation.

FIGS. 16 through 18 are perspective views of a portion of a spinal column 30. Spinal column 30 includes a plurality of vertebrae 40 with spinous processes (e.g., 100 and 110). Spinal column 30 also includes the spinal cord and nerve roots (not shown for clarity). In one embodiment the apparatus can be implanted to increase the volume and/or cross sectional area of spinal canal thereby alleviating restrictions on vessels and nerves 60 associated therewith, and reducing pain caused by such restrictions.

For purposes of implantation between adjacent first and second spinous processes 100 and 110 of spinal column 30 (see FIGS. 16 through 18), adjustable implant 200 can be configured as shown in FIGS. 1 through 43. First and second spinous processes 100 and 110 are exposed using appropriate surgical techniques and thereafter, adjustable implant 200 is positioned so that upper wedging member 700 engages first spinous process 100, and lower wedging member 900 engages second spinous process 110 (e.g., see FIGS. 15, 18). At this point, wedging members 700, 900 can be caused to expand respectively in the directions of arrows 702 and 902 (e.g., see FIG. 18) by manipulation of control screw 1500 with tool 4030. Such expansion spreads apart or distracts spinous processes 100 and 110 with the beneficial effect of enlarging the volume and/or cross sectional area of the spinal canal in order to alleviate restrictions on blood vessels and nerves.

Figure 1:
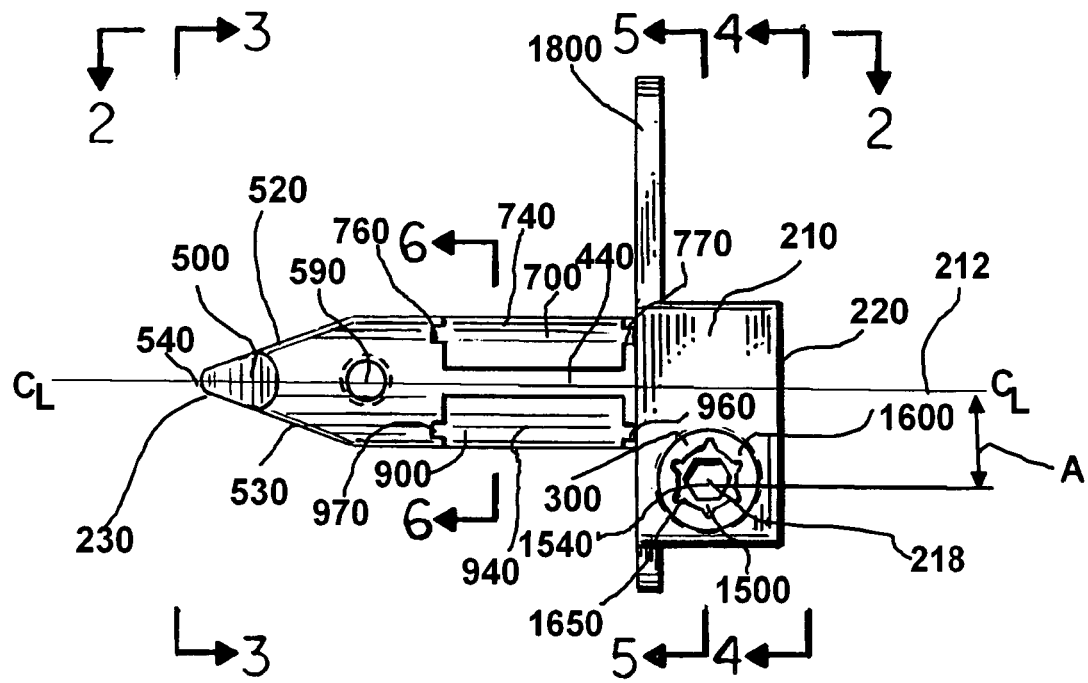
FIG. 1 is an elevation view of the preferred embodiment of the apparatus of the present invention.
Figure 2:
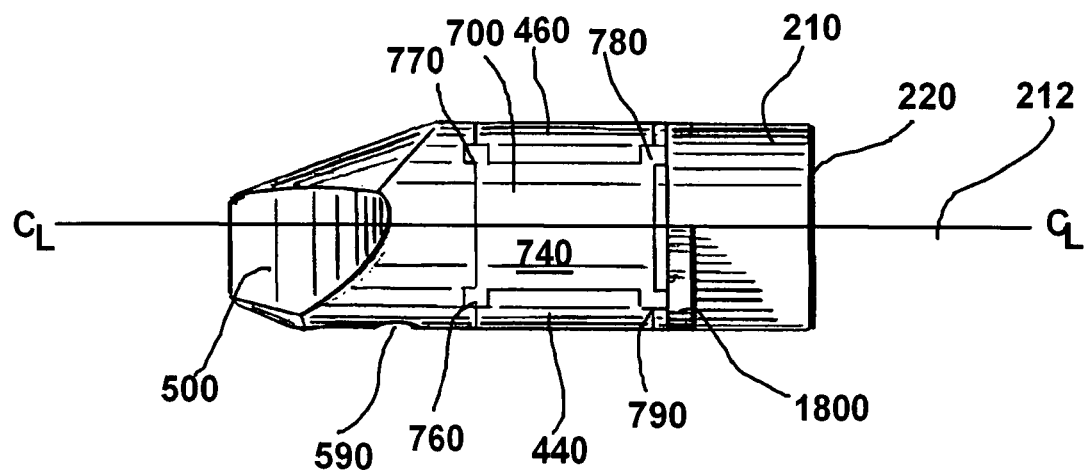
FIG. 2 is a top view of the preferred embodiment of the apparatus of the present invention showing the body portion of an adjustable implant, taken along lines 2-2 of FIG. 1.

Generally, adjustable implant can comprise body 210 along with first and second wedging members 700 and 900 (see, e.g., FIG. 1). First and second wedging members can be mechanically expanded in the respective directions (and retracted in the opposite directions) of arrows 702 and 902. As will be described below first and second wedging members 700 and 900 can be operatively connected to adjusting screw or worm gear 1200. In one embodiment, when adjusting screw 1200 is turned in a first direction (e.g., in the direction of arrow 214 in FIG. 4, and in the direction of arrow 1556 in FIG. 7) wedging members 700 and 900 expand or move respectively in the directions of arrows 702 and 902. When adjusting screw 1200 is turned in the opposite direction (i.e., in the opposite direction of arrow 214 in FIG. 4 and arrow 1556 in FIG. 7) wedging members 700 and 900 retract or move respectively in the opposite directions of arrows 702 and 902. For both expansion and retraction, a controlled change in the state of expansion or retraction can be obtained through the use of a worm gear on adjusting screw 1200.

Figure 15:
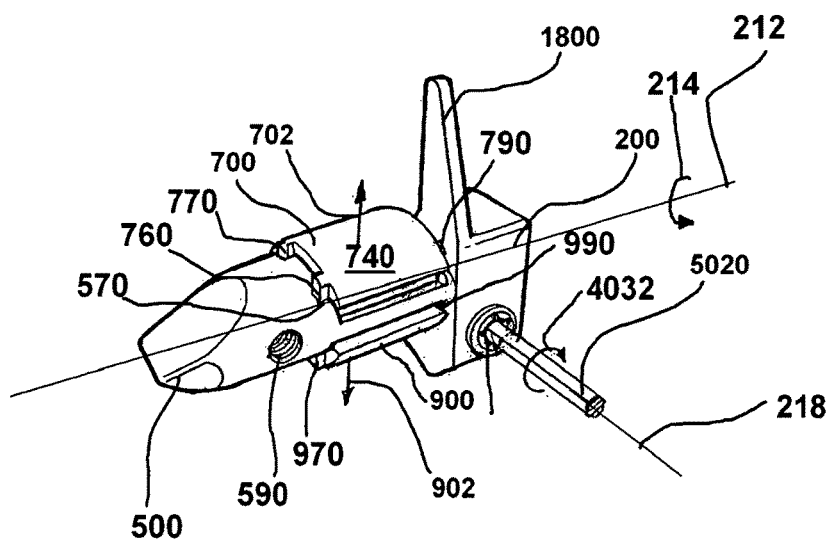
FIG. 15 is a partial perspective view of the preferred embodiment of the apparatus of the present invention showing adjusting of the control.

In FIGS. 7 and 15, an expanded position of wedging members 700 and 900 is shown. In FIGS. 1, 2, 6, 11, and 14 a retracted or collapsed position of wedging members 700, 900 can be seen. The amount of expansion (or contraction) of wedging members 700 and 900 can be controlled by adjusting screw 1200 and control screw 1500.

In one embodiment a control screw 1500 can be operatively connected to adjusting member 1200 such as by a worm gear connection. Control screw 1500 can be placed in bore 300 of body 210 (e.g., FIG. 5 where bore 300 is not threaded) and operatively connected to gear teeth or threads 1260 of adjusting screw 1200 through opening 320 of body 210. As control screw 1500 is turned in the direction of arrow 4032 (see FIG. 5), adjusting screw 1200 will move in the direction of arrow 214. On the other hand, as control screw 1500 is turned in the opposite direction of arrow 4032 (see FIG. 5), adjusting screw 1200 will move in the opposite direction of arrow 214. Turning of adjusting screw 1200 causes wedging members 700 and 900 to move: (a) respectively in the directions of arrows 702 and 900 or (b) respectively in the opposite directions of arrows 702 and 902, each case depending on the relative direction of adjusting screw 1200 or gear.

By controlling the expansion or retraction of wedging members 700 and 900, a surgeon can control the amount of distraction caused by wedging members 700 and 900 upon a pair of spinous processes where adjustable implant 200 is placed in between. Such control can allow a surgeon to use a single adjustable implant 200 to properly distract spinous processes 100 and 110 of multiple sizes and configurations (see e.g., FIGS. 16-18). In prior art devices, such controlled amount of distraction is not available and spinous processes 100 and 110 of different sizes or configurations require multiple sizes of distraction implants.

With prior art distraction implants the surgeon may not be able to tell the proper size of the prior art distraction implants required for a particular set of spinous processes 100 and 110, and will select a first prior art implant of a first size and attempt to implant same and realize that the desired amount of distraction is not obtained (because the selected prior art Implant is too small) or that too much distraction is obtained (because the selected prior art implant is too large). If the distraction amount is too small the surgeon will have to remove the selected prior art implant and select a different prior art implant (of larger size) hoping that this second implant will provide an appropriate amount of distraction. This slows down the implantation process and unnecessarily aggravates the tissue and bony area around spinous processes 100 and 110. If the distraction amount is too large (beyond having to implant a second implant) damage may actually occur from excessive distraction.

FIGS. 1-15 show more particularly the construction of adjustable spine distraction implant 200. A body/housing 210 provides first 220 and second 230 end portions. A gear case or body 210 has a dual diameter socket that includes large internally threaded bore 330 and smaller non-threaded bore 300. Bore 300 is receptive of control screw 1200. Bore 330 is receptive of threaded locking screw or nut 1600. As shown in FIG. 5, the locking screw 1600 on the upper end, and base 310 on the lower end limits the amount of vertical movement (schematically indicated by arrow 1558 of FIG. 5) of control screw 1500 thus allowing control screw 1500 to rotate adjusting screw or gear 1200 and finally expand or retract wedging members 700 and 900.

Figure 8:
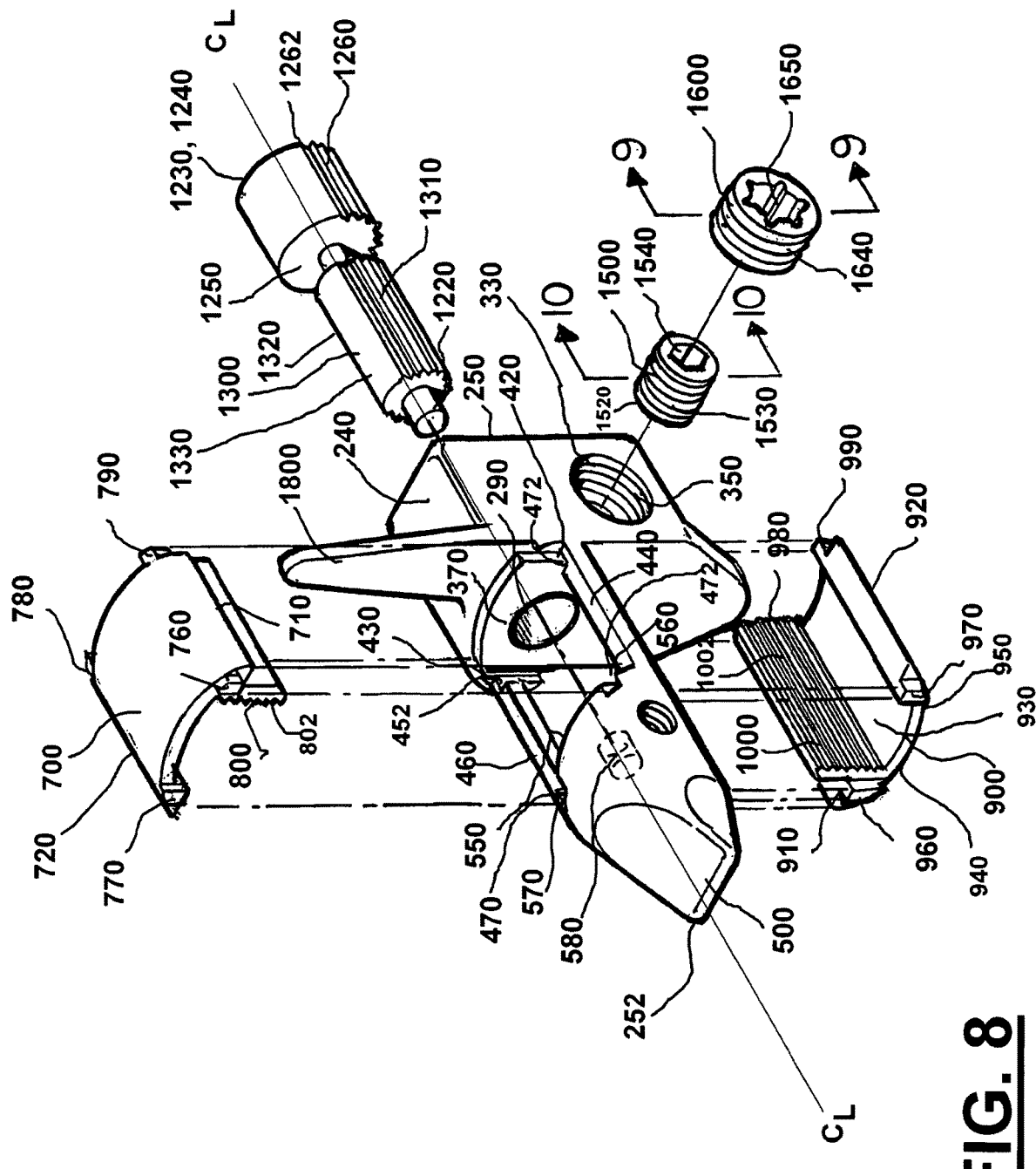
FIG. 8 is a perspective exploded view of the preferred embodiment of the apparatus of the present invention.
Figure 9:
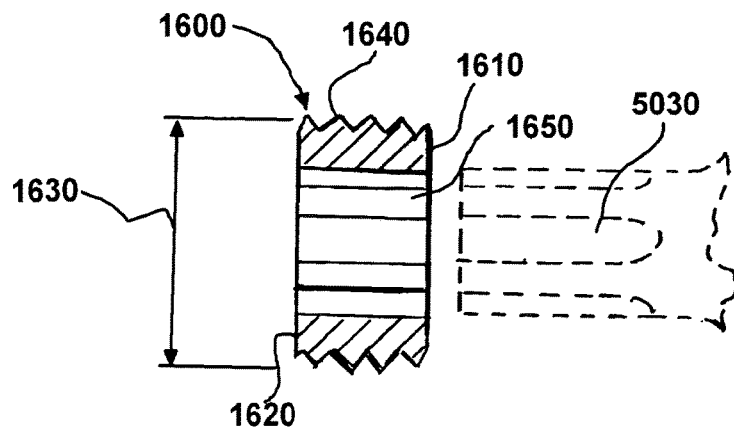
FIG. 9 is a fragmentary sectional view of the preferred embodiment of the apparatus of the present invention showing the threaded cap.
Figure 10:
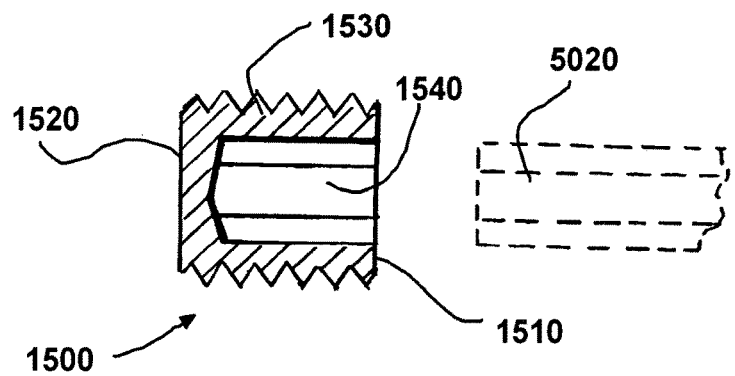
FIG. 10 is a sectional view of the adjusting screw.

As shown in FIGS. 8 and 10, control screw 1500 can have a tool (e.g. alien wrench) receptive socket 1540 that is receptive of a tool end 5020 and external thread 1530. The tool end portion 5020 of tool 5120 interlocks with socket 1540 (e.g. alien wrench receptive) of threaded control screw 1500. As shown in FIGS. 8 and 9, locking screw or nut 1600 can have a tool (e.g. star) receptive socket 1650 that connects with tool 5030. The tool end portion 5030 interconnects with socket (e.g. star drive) 1650 of locking screw or nut 1600. Locking screw or nut 1600 can have external threads 1640.

Tool 5020 can be used to turn control screw 1500 which in turn rotates adjusting screw 1200 which in turn expands or retracts wedging members 700 and 900. Tool 5030 can be used to frictionally lock control screw in place and prevent further movement of adjusting screw 1200 or wedging members 700 and 900.

After locking screw or nut 1600 is loosened, second tool or driver 5020 can be used to rotate control screw 1500 and thus rotate adjusting screw or gear 1200 in a selected direction (such as that indicated by arrow 214 in FIG. 5, or in the opposite direction of arrow 214). As shown in FIGS. 4, 5, and 8, adjusting screw or gear 1200 can be rotatively connected to body 210 through first longitudinal bore 270 and longitudinal bore 580. Second end 1220 of adjusting screw or gear 1200 is supported by and rotates in longitudinal bore 580 while head 1230 rotates in and is supported by first longitudinal bore 270.

FIGS. 5 and 8 shows one embodiment of adjusting screw 1200 being operably connected to wedging members 700 and 900, and how control screw 1500 can be operably connected to adjusting screw 1200 thereby making control screw 1500 operably connected to wedging members 700 and 900. FIG. 6 is a schematic view of adjustable implant 200 where wedging members 700 and 900 are in a retracted state. FIG. 7 is a schematic view showing wedging members 700 and 900 in a partially to completely extended or expanded state.

FIGS. 4, 6, 7, and 18 schematically show that, as adjusting screw 1200 rotates in the direction of arrow 214 (or from the opposite view in the direction of arrow 1556 shown in FIG. 7), wedging members 700 and 900 respectively move in the directions of arrows 702 and 902. Similarly, if rotation is in the opposite direction of arrow 214 (or in the opposite direction of arrow 1556 in FIG. 7), wedging members 700 and 900 move respectively in the opposite directions of arrows 702 and 902. As shown in FIGS. 6 through 8, middle section 1300 of adjusting screw or gear 1200 can be operatively connected to arm 800 of wedging member 700 through threaded or gear toothed area 1310 cooperating with threaded arm 800. Middle section 1300 of adjusting screw or gear 1200 can be operatively connected to arm 1000 of wedging member 900 through threaded or gear toothed area 1320 cooperating with threaded arm 1000. Such a threaded or gear toothed connection can be referred to as a rack and pinion type connection. Additionally, as shown in FIG. 5 control screw 1500 can be operatively connected to adjusting screw or gear 1200 by means of threaded or gear toothed area 1260 of adjusting screw or gear 1200. Such a threaded or gear toothed connection can be referred to as a worm gear type connection.

Wedging members 700 and 900 can be slidably connected to body 210 of adjustable implant 200 through a series of pins and tracks. As shown in FIGS. 6 through 8 body or gear box 210 can be comprised of first end 250 and second end 252. Guide 500 can be connected to body 210 by first and second longitudinal arms 440 and 460. First end 250 can have a raised portion 370 and guide 500 on second end 252 can include a base 550. As shown in FIG. 8, raised portion 370 can include track 420 and track 430. Also as shown in FIG. 8 base 550 can include track 560 and track 570. Opposed tracks 420, 430, 560, and 570 can form a three dimensional track system for wedging members 700 and 900 to slide back and forth in (as schematically indicated in FIGS. 6, 7, 15, and 18.

Adjustment screw 1200 can be rotatively connected to body 210 through bore 270 in second end and bore 580 in guide 500. Tip 1220 can rotatively sit in bore 580 and head 1230 can rotatively sit in bore 270.

In one embodiment body 210 can include a cover for head 1230 which would prevent adjusting screw 1200 from coming out of body or gear box 210. Although not shown in another embodiment to prevent adjustment screw from falling out of body 210 wherein a threaded or gear toothed area 1260 can extend a length 1270 from top 1240 of head 1240 to a point before reaching the base 1250, after which point non-threaded area 1230 of head 1230 will be found. Control screw 1500 will threadably engage the threaded portion 1260 of adjustment screw 1100, but control screw 1500 will resist longitudinal movement of adjustment screw 1200 by threads 1530 contacting the non-threaded area 1230 of adjustment screw 1200 and not allowing longitudinal movement.

As shown in FIGS. 1,2, 6-8, 11, 14, and 15, wedging members 700 and 900 can be constructed substantially identical. Wedging member 700 can be substantially identical to wedging member 900 but essentially rotated one hundred and eighty degrees so that the bottom 720 of wedging member 700 is in line with the top 910 of wedging member 900. Each of the wedging members 700, 900 can respectively be provided with a gear panel or arm 800, 1000 having a threaded or toothed rack 802, 1002. Wedging member 700 has gear panel or arm 800 with toothed rack 802. Wedging member or plate 900 has gear panel or arm 1000 with toothed rack 1002. Therefore, only the construction of wedging member 900 will be described in detail. Wedging member 900 can comprise top 910, bottom 920, interior portion 930, exterior portion 940, curved portion 950. Wedging member 900 can also include threaded or gear toothed arm 1000 and four rails or prongs 960, 970, 980, and 990.

Looking at FIGS. 6 through 8, and 15 through 18, it can be seen that wedging member 900 can be slidably connected to body 210 through its rails or prongs 960 and 970 slidably connecting to slots 570 and 560 of the base 550 of guide 500; and through its rails or prongs 990 and 980 slidably connecting to slots 430 and 420 of raised area 370. The four rails or prongs of wedging member 900 can maintain a straight path for wedging member sliding in the slots of raised area 370 of body 210, and base 550 of guide 500. Similarly the rails or four prongs of wedging member 700 can maintain a straight path for wedging member sliding in the slots of raised area 370 of body 210, and base 550 of guide 500. The extent of expansion and retraction of wedging members 700 and 900 can be controlled by threaded area 1310 cooperating with threaded arm 800 of wedging member 700, and threaded area 1320 cooperating with threaded arm 1000 of wedging member 900. In this manner wedging members 700 and 900 can be held in place at a selected amount of expansion or contraction (regardless of where they have been expanded or retracted to) as long as wedging members' 700 and 900 prongs remain at least partially sitting in the specified slots.

Each wedging member 700 or 900 can maintain a straight (generally vertical) path for wedging member 700, 900 sliding in the slots 420, 430, 560, and 570. The extent of expansion and retraction of wedging members/plates 700 and 900 can be controlled by screw/gear 1200. In this manner plates/wedging members 700 and 900 can be held in place at a selected amount of expansion or contraction (regardless of where they have been expanded or retracted to) as long as wedging members' 700 and 900 rails 760, 770, 780, 790 (for wedging member 700) and rails 960, 970, 980, and 990 (for wedging member 900) remain at least partially sitting in the specified slots.

To ensure that the prongs remain at least partially in the slots, the radial extent of threading for threaded areas 1310 and 1320 can be selected by having non-threaded areas 1330 and 1340. That is when the radial extent of the threaded area is reached, the specific wedging member (700 and/or 900) will stop its expansion. As shown in FIG. 4, a second safe guard can be provided in the amount of radial threading 1260 for the worm gear portion of adjusting screw 1200. In a preferred embodiment, an angular amount 1280 of about 120 degrees of radial threading 1260 can be provided which will restrict further rotation of screw 1200—when the threads angularly reach point 1262 or 1264 (see FIG. 5).

As shown in FIG. 8 arms 440 and 460 can include notches 450, 452, 470, and 472 to accommodate the rails or prongs of wedging members 700 and 900, and allow complete retraction of wedging members 700 and 900. Without these notches the prongs of wedging members 700 and 900 would prevent complete retraction.

Figure 11:
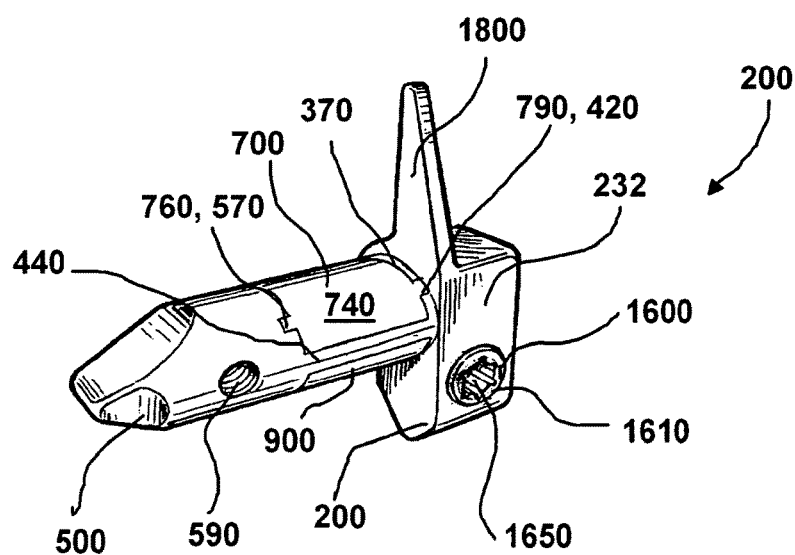
FIG. 11 is a partial perspective view of the preferred embodiment of the apparatus of the present invention.

FIG. 11 is a perspective view of adjustable implant 200 placed on its side. In this embodiment wedging members 700 and 900 are completely retracted and their exterior surfaces 740 and 940 are flush with raised area 370 of second end 220 and base 550 of guide 500. Making the exterior surfaces flush when wedging members 700 and 900 are fully retracted resists damage to bone and tissue during the initial insertion process (as no sharp edges are seen).

After the desired or proper expansion or retraction is obtained with wedging members 700 and 900, control screw 1500 can be locked in place by locking screw 1600. Locking screw 1600 can include first end 1610, second end 1620, and threaded area 1640. Locking screw 1600 can have bore 1650 which allows access to control screw 1500 even when locking screw 1600 is connected to the bore 330 for locking screw 1600. Bore 1650 allows locking screw to be in place even when adjusting control screw 1500. This feature reduces the amount of free parts the surgeon must keep track of during the operation (and prevents control screw 1500 and locking screw 1600 from falling out during an implantation procedure). In one embodiment a cover for bore 330 can be provided which prevents locking screw 1600 from being completely removed from body 210. After the desired amount of distraction is obtained, preferably, control screw 1500 is locked in place by second end 1620 of locking screw 1600 squeezing control screw 1500 against base 210 of bore 300. This squeezing frictionally locks in place control screw 1500. Even if not frictionally locked by locking screw 1600, the status of being a worm gear connection between control screw 1500 and threads 1260 of adjustment screw 1200, would tend to be self locking. However, without locking screw 1600, vibrations and other movements of implant 200 over time may tend to cause adjustment screw 1200 to rotate and cause unwanted movement of wedging members 700 and 900. Preferably, when locking screw 1600 is locked in place, first end 1610 is flush with top 232 of body 210.

Adjustable implant 200 and its components can be made of a number of materials, including but not limited to, stainless steel, titanium, ceramics, plastics, elastics, composite materials or any combination of the above. In addition, the modulus of elasticity of the implant can be matched to that of bone, so that the implant is not too rigid. The flexibility of the implant can further be enhanced by providing additional apertures or perforations throughout the implant.

Preferably, adjustable implant provides for distraction in the range of about 8 mm to about 11 mm in one embodiment (more preferably about 8 mm to about 10.7 mm), and in another embodiment in the rage of about 10 mm to about 15 mm (more preferably about 10.5 mm to about 14 mm).

In one embodiment an implantation guide 500 can be provided. Positioned at the other end of body 210 can be guide 500. Guide 500 can be triangularly-shaped so as to be a pointed and arrow-shaped guide. Alternatively, guide 500 can be in the shape of a cone with lateral truncated sides along the longitudinal axis wedging members 700 and 900. Guide 500 can include a threaded bore 590. In other embodiments guide 500 can be bulbous, cone-shaped, pointed, arrow-shaped, and the like, in order to assist in the insertion of adjustable implant 200 between adjacent spinous processes. Preferably, the insertion technique disturbs as little of the bone and surrounding tissue or ligaments as possible in order to (a) reduce trauma to the site and facilitate early healing, and (b) not destabilize the normal anatomy. In various embodiments there is no requirement to remove any of the bone of the spinous processes and depending on the anatomy of the patient, there may be no requirement to remove or sever ligaments and tissues immediately associated with the spinous processes.

In one embodiment guide 500 has a cross-section which is adjacent to the cross section of completely retracted wedging members 700 and 900 and of similar shape. Where guide 500 and completely retracted wedging members 700 and 900 have elliptical cross sections, preferably the major dimension of guide's 500 cross section is about equal to the major dimension of completely retracted wedging members 700 and 900 cross section, and guide's 500 minor dimension about equal to completely retracted wedging members 700 and 900 cross section. In this embodiment, guide 500 can extend from body 210 of implant 200 with a cross-section which reduces in size in a direction away from body 210. In another embodiment, guide 500 can be cone-shaped with a base located adjacent wedging members 700 and 900. Further, in one embodiment guide 500 can have a base cross-section about the same as an oval cross-section of completely retracted wedging members 700 and 900.

In one embodiment guide 500 has faces 520 and 530 which are at about 45 degree angles (other angles, such as by way of example only, from about 30 degrees to about 60 degrees, and from about 25 to about 75 degrees are also envisioned), with a tip 540 so that adjustable implant 200 can be more easily urged between the spinous processes.

In one embodiment, adjustable implant 200 can have a central body portion, the central body portion including wedging members 700 and 900, with a longitudinal axis 212. Extending from the central body portion can be a first wing 1800 and second wing 2000 which can be substantially perpendicular to longitudinal axis 212. Wings 1800 and 2000 can resist the tendency of adjustable implant to slide out from between spinous processes 100 and 110. In one embodiment second wing 2000 can detachably connectable to adjustable implant 200. In one embodiment second wing 2000 can be laterally adjustable relative to first wing 1800 to accommodate spinous processes of varying sizes and dimensions—arrows 2002 and 2004 in FIG. 17 schematically indicate lateral adjustment of second wing 2000. Making wing 2000 detachably connectable facilitates insertion of adjustable implant between spinous processes 100 and 110, such as through guide 500.

In one embodiment, completely retracted wedging members 700 and 900 can have an elliptical cross section with a major axis which is substantially perpendicular to a major dimension (e.g., longitudinal axis) of first wing 1800 along longitudinal axis. Making these two axes substantially perpendicular facilitates proper positioning of adjustable implant 200 between selected spinous processes 100 and 110, and ensuring that substantial portions of wedging members 700 and 900 come in contact with both the upper and lower spinous processes so that the reaction loads can be more evenly distributed on the spinous processes by wedging members 700 and 900 during implantation and subsequent spinal column movements after implantation.

Wings 1800 and 2000 which are not perpendicular to longitudinal axis 212 are envisioned, and can be offset by 5, 10, 15, 20, and/or 25 degrees from the perpendicular and/or any range without such amounts. As shown in FIG. 3, first wing 1800 can include an upper area 1830 and a lower area 1840. Upper area can include a rounded end 1832. Rounded end 1832 can be designed to accommodate the anatomical form or contour various portions of the vertebrae, for example L4 (for a L4-L5 placement) or L5 (for a L5-S1 placement) superior lamina of the vertebra. It is to be understood that the same shape or variations of this shape can be used to accommodate other lamina of any vertebra. The lower portion 1842 can also be rounded in order to accommodate the vertebrae.

In one embodiment guide 500 can include a threaded bore 590 which accepts a screw 2130 in order to hold a second wing 2000 in position. With the second wing 2000 in position, the screw 2130 when it is positioned in the threaded bore 590 can engage and hold second wing 2000 in position relative to first wing 1800.

First and second wings 1800 and 2000 can come in a variety of shapes in order to provide for variations in the anatomical form of the spinous processes. Such shapes can be as depicted in FIGS. 103, 104, 105, 106, and 107 of U.S. Pat. No. 7,101,375. In these configurations, the wing has an upper portion and a lower portion. In FIG. 104, the lower portion is thicker than the upper portion in order to accommodate the spinous process, where the lower spinous process is thinner than the upper spinous process. In FIG. 105, both the upper and lower portions are enlarged over the upper and lower portions of FIG. 103 to accommodate both the upper and lower spinous processes being smaller. That is to say that the space between the upper and lower portions of the first and second wings are reduced due to the enlarged upper and lower portions of the second wing. Alternative embodiments of second wings 2000, as shown in FIGS. 104 and 105, are depicted in FIGS. 106 and 107. In these FIGS. 106 and 107, the second wing accommodates the same anatomical shape and size of the spinous processes as does the second wing in FIGS. 104 and 105 respectively. However, in the embodiments of the second wing of FIGS. 106 and 107, substantial masses have been removed from the wings. The upper and lower portions are essentially formed or bent in order to extend from the central portion of the second wing.

Figure 12:
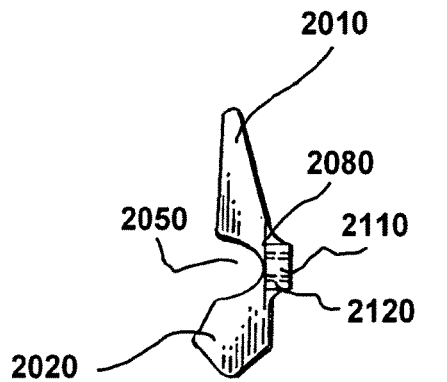
FIG. 12 is a fragmentary view showing second fixture or wing.
Figure 13:
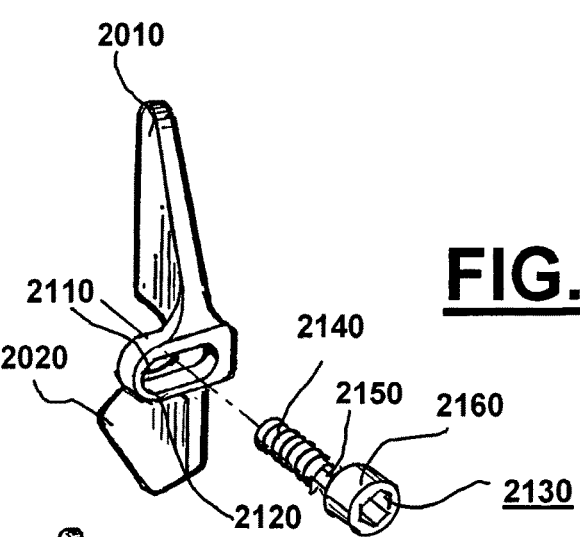
FIG. 13 is a fragmentary view of second fixture or wing.
Figure 14:
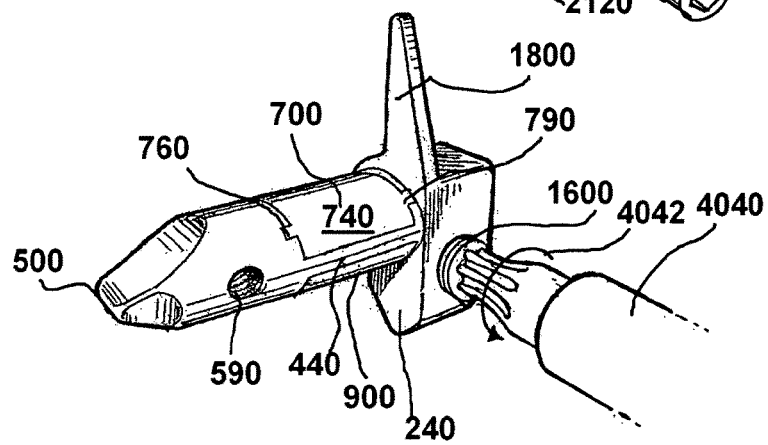
FIG. 14 is a partial perspective view of the preferred embodiment of the apparatus of the present invention.

FIGS. 12 and 13 are views of second wing 2000 and connecting screw 2130. Connecting screw 2130 can comprise threaded area 2140 and reduced cross sectional area 2150. Reduced cross sectional area 2150 can allow second wing member 2000 to slide (and be longitudinally adjustable) relative to screw 2130 (and first wing member 1800). Second wing member 2000 can include track 2110 and track can include threaded area 2120. Second wing member 2000 can include first end 2010, second end 2020, and cutout area 2050. Cutout area 2050 can be shaped to fit around the outer surface of guide 500. Alternatively, cutout area 2050 can be enlarged to allow full distraction of wedging members 700 and 900 (see e.g., FIG. 35 with second wing 2000''' and cutout area 2050''').

FIG. 15 is a perspective view of adjustable implant 200 having first and second wedging members 700 and 900 extended in the directions of arrows 702 and 902 and control screw 1500 being turned in the direction of arrow 4032, causing adjusting screw or gear 1200 to turn in the direction of arrow 214 along longitudinal centerline 212.

FIG. 17 is a perspective view of adjustable implant 200 placed in between spinous processes 110 and 120. Preferably a longitudinal line 2008 through second wing 2000 will be parallel to a longitudinal line 1808 going through first wing 1800. Arrows 2002 and 2004 schematically indicate the adjustability of second wing 2000 relative to first wing 1800 by varying the distance D.

FIG. 18 is a side perspective view of adjustable implant 200 showing a tool 4030 being used on the control screw 1500 to adjust adjusting screw 1500 and change the state of first 700 and second 900 wedging members. In FIG. 18 is shown both line 212 (which is the axis of rotation of adjusting screw or gear 1200) and a line 218 which is perpendicular to the axis of rotation of control screw 1500 (schematically indicated by arrow 4032). As shown in FIG. 1, line 218 can be spaced apart by the distance A from the axis of rotation of control screw 1500. As can be seen the axis of rotation of control screw 1500 does not intersect the axis of rotation of adjusting screw or gear 1200.

Adjustable implant 200 can be positioned adjacent to upper and lower vertebrae 120 and 130. Extending upwardly from vertebrae 120 and 130 are the upper and lower spinous processes 100 and 110. In a preferred embodiment, the fit of adjustable implant 200 between spinous processes 100 and 110 can be such that wings 1800 and 2000 do not touch spinous processes 100 and 110. One advantage of wings 1800 and 2000 is that they resist dislodgment of adjustable implant 200 from between spinous processes 100 and 110.

Preferably, during the surgical process first and second wedging members 700 and 900 of adjustable implant 200 are urged between spinous processes 100 and 110. After this has occurred, second wing 2000 can be guided by the other sides of the spinous processes from a path which causes the plane of second wing 2000 to move substantially parallel to the plane of first wing 1800 until screw 2130 can be placed in threaded bore 590 of guide 500. Bolt 2130 can be tightened to secure second wing 2000.

In one embodiment a second wing 2000 is not used where it was deemed impractical or unnecessary to use a second wing 2000.

In one embodiment neither a first 1800 nor a second 2000 wing is used where the anatomy between the spinous processes 100 and 110 was such that it would be undesirable to use either a first or second wing.

In one embodiment the spinous processes 100 and 110 can be accessed and distracted initially using appropriate instrumentation, and adjustable implant 200 can be inserted and adjusted in order to maintain and achieve the desired distraction. In another embodiment the spinous process can be accessed and adjustable implant 200 appropriately positioned. Once positioned, implant 200 can be expanded in order to distract the spinous processes or extend the distraction of already distracted spinous processes. Accordingly, adjustable implant 200 can be used to create or increase a previously created distraction, or to maintain a distraction which has already been created.

FIGS. 19-23 show an instrument or tool 5000 that can be used to rotate either the control screw 1500 and/or the locking screw/nut 1600 and adjust adjustable implant 200. Tool 5000 can include body 5010, shaft 5014, control screw head 5020, locking screw head 5030, driver 5120, driver 5130, counter torque handle 5200, base 5300, and set prongs 5310, 5320. Torque handle 5200 can be connected to body 5010 and enables a surgeon to hold and support the tool/instrument 5000. Driver 5130 can be slidingly and rotatively connected to body 5010. Driver 5130 can include locking screw head 5030. Driver 5120 can be slidingly and rotatively connected to driver 5130. Driver 5120 can include control screw head 5020. Driver 5130 can be connected to shaft 5134 which itself is connected to locking screw head 5030. Base 5300 can be connected to body 5010 and include two set prongs 5310 and 5320. Set prongs 5310 and 5320 can locate or set tool 5000 relative to body 210 of adjustable implant 200 by matching set prongs 5310 and 5320 with openings 5310' and 5320'. Once set the individual drivers 5120 and 5130 can be used to drive control screw head 5020 and locking screw head 5030 which respectively will turn control screw 1500 and locking screw 1600. Arrows 5121 and 5122 schematically indicate slidable movement of driver 5120. Arrow 5017 schematically indicates rotation of driver 5120 (which can also be in the opposite direction). Arrows 5015 and 5016 schematically indicate slidable movement of driver 5130.

Arrow 5017 schematically indicates rotation of driver 5130 (which can also be in the opposite direction). Tool 5000 is a preferred tool in that it allows both control screw 1500 and locking screw 1600 to be manipulated with a single instrument. Additionally, it can optionally have a placement system (body 5300 and prongs 5310 and 5320). Body 5300 can be a distal flange or bracket that carries one or more projections or prongs 5310 and 5320. If the optional body 5300 is employed, the gear case or body 210 carries sockets 5310' and 5320' that are sized and shaped correspondingly to projections 5310 and 5320. In this fashion, the surgeon can interlock the projections 5310 and 5320 with the sockets 5310' and 5320' to help rigidify the connection of the tool or instrument 5000 to the body or gear case 210 when an adjustment of either of the screws 1500 or 1600 is required.

FIGS. 24-27 show another embodiment of the apparatus of the present invention, designated by the numeral 200A. The embodiment of FIGS. 24-27 is basically the same as the embodiment of FIGS. 1-23. However, the first and second fixtures or wings 1800', 2000' are respectively provided with prongs or projections or spikes 1872, 1882 which enhance gripping of the spine 30 (and spinous processes 100 and 110).

FIGS. 28-30 show another embodiment of the apparatus of the present invention, designated generally by the numeral 200B. In FIGS. 28-30, the implant 200B is similar in construction to the embodiment of FIGS. 1-23 with the exception of the shape of the wings 1800", 2000" being generally rectangular, but also providing rounded or curved end portions. The first wing 1800" provides upper and lower rounded or curved end portions 1830", 1840". The second wing or fixture 2000" provides upper and lower rounded or curved end portions 2030", 2040". As with the preferred embodiment, the second fixture or wing 2000" provides a concavity 2050" that is receptive of body 210. As with the preferred embodiment, a fastener 2130 enables attachment of second fixture or wing 2000" to body 210 using fastener 2130 with a track/slot 2110" as with the embodiment shown in FIG. 13. In one embodiment concavity 2050" can be expanded to allow wedging members 700 and 900 to be fully distracted even where second wing 2000" is placed over wedging members 700 and 900.

FIGS. 31-32 show yet another embodiment, designated generally by the numeral 200C. Adjustable implant 200C provides the same basic construction of the embodiment of FIGS. 1-18 with the addition of a flexible sleeve 2500 that is placed over the body 210 (and wedging members 700 and 900) as shown in FIGS. 31 and 32. The sleeve 2500 has a hollow bore or open ended cavity 2510 that enables the sleeve 2500 to occupy a position on body 210, basically covering wedging members 700 and 900, when the wedging members/plates 700 and 900 are expanded or retracted, the sleeve acts as an interface or cushion in between the wedging members 700 and 900 and the surrounding tissue. This can prevent pinching, tearing, or damage to the surrounding tissue.

FIGS. 33 through 43 show one embodiment for laterally adjusting the second wing relative to the first wing with another embodiment of second wing 2000'''. FIGS. 36-43 show an instrument or tool 6000 that can be used to slidingly adjust/clamp second wing 2000''' relative to first wing 1800''' of various adjustable implants. Tool 6000 can include body 6010, shaft 6014, wing fastener screw head 6020, sliding adjuster screw head 6030, driver 6120, driver 6130, counter torque handle 6200, base 6300, and set prongs 6310, 6320. Torque handle 6200 can be connected to body 6010 and enables a surgeon to hold and support the tool/instrument 6000. Driver 6130 can be slidingly and rotatively connected to body 6010. Driver 6130 can include sliding adjuster screw head 6030. Driver 6120 can be slidingly and rotatively connected to driver 6130. Driver 6120 can include fastener screw head 6020. Base 6300 can be connected to body 6010 and include two set prongs 6310 and 6320. Set prongs 6310 and 6320 can locate or set tool 6000 relative to second wing 2000''' of adjustable implant 200 by matching set prongs 6310 and 6320 with openings 6310' and 6320'. Once set the individual driver 6130 can be used to slidingly adjust second wing 2000''' relative to first wing (for a clamping effect) of adjustable implant 200. When the proper adjustment between the two wings is achieved, driver 6120 can be used to lock fastener 2130 with control screw head 6020. By adjusting second wing 2000''' closer to the other wing (in a clamping motion), the two wings can grab hold of and/or bite into spinous processes 100 and 110 to resist relative movement between the adjustable implant and the spinous processes. Arrow 6017 schematically indicates rotation of driver 6130. Arrows 6018 schematically indicate movement of second wing 2000''' in a clamping motion (relative to first wing 1800 which is not shown). Body 6300 can be a distal flange or bracket that carries one or more projections or prongs 6310 and 6320. If the optional body 6300 is employed, the second wing 2000''' carries sockets 6310' and 6320' that are sized and shaped correspondingly to projections 6310 and 6320. In this fashion, the surgeon can interlock the projections 6310 and 6320 with the sockets 6310' and 6320' to help rigidify the connection of the tool or instrument 6000 to the second wing 2000''' before adjustment of second wing relative to the adjustable implant to obtain a clamping motion. After head 6030 is inside of well 2112''' and attached to gear teeth or threads 2120''' second wing 2000''' will slide along adjustable implant via opening 2050''' sliding over adjustable implant. In one embodiment the amount of adjustment of second wing 2000''' is limited so that this wing does not travel over wedge members 700 and/or 900.

Projections or prongs 1882 help stabilize adjustable implant relative to the spinal processes. In one embodiment opening 2050''' can be enlarged to allow full expansion/distraction of wedging members 700 and 900 even where second wing 2000''' is adjusted over wedging members 700 and 900.

Various alternative embodiments or options for any of the above described will be described below.

In one embodiment adjustable implant 200 can act as an extension stop. For example, adjustable implant can resist or stop further extension between spinous processes 100 and 110 once the back has been bent backwardly such that adjustable implant 200 stops further movement of adjacent spinous processes 100 and 110 towards each other. The distance between wedging members 700 and 900 can stop movement spinous processes 100 and 110 toward each other. Adjustable implant 200 does not limit the flexion of spinal column 30 (because in flexion spinal column 30 is bent forwardly and spinous processes 100 and 110 move away from each other (and away from wedging members 700 and 900).

In one embodiment only one wedging member 700 is provided. In this embodiment wedging member 900 can be permanently attached to body 210 (and arm 100 either removed entirely or the threading removed). In this embodiment wedging member can expand or retract based on movement of adjustment screw 1200. In this embodiment about one half of the adjusting expansion or distraction capability will be available compared to embodiment where two wedging members 700 and 900 are provided.

In one embodiment only one longitudinal arm 440 is provided. The shape of wedging members 700 and 900 can be adjusted to compensate for forming an elliptical cross section when completely retracted.

Although not shown, in one embodiment only one adjustable wedging member or plate 700 (or 900) is provided. In this embodiment it is expected that only one half of the adjustability of a two wedge/plate member will be provided.

Although not shown, in one embodiment a cap can be placed over first longitudinal bore 270 which also will prevent adjusting screw 1200 from leaving first longitudinal bore 270. This cap can also prevent adjustable implant 200 from being disassembled after manufacture which can prevent improper reassembly. This cap can be laser welded to body 210. In one embodiment one or more timing marks can be placed on adjusting screw 1200 (e.g., its head 1230) and body 210 which marks can show proper alignment of adjusting screw 1200 relative to body 210 (ensuring proper installation of the components).

Although not shown, in one embodiment one or more raised areas or detents can be included on first wing 1800 which can limit the expansion of wedging members 700 and/or 900. These raised areas or detents can act as an additional factor of safety beyond the various amounts of threading on adjusting screw 1200 (middle section 1300 and head 1230).

In one embodiment wedging members 700 and 900 have a flat, irregular, or concave shape.

Surgical Method

With all the ligaments (such as the superspinous ligament) and tissues associated with the spinous processes left intact, adjustable implant 200 can be implanted essentially floating in position in order to gain the benefits of extension stop and not limiting flexion. In one embodiment the spinous processes can be accessed and distracted initially using appropriate instrumentation, and adjustable implant 200 can be inserted and adjusted in order to maintain and achieve the desired distraction. In another embodiment the spinous process can be accessed and adjustable implant 200 appropriately positioned. Once positioned, implant 200 can be expanded in order to distract the spinous processes or extend the distraction of already distracted spinous processes. Accordingly, adjustable implant 200 can be used to create or increase a previously created distraction, or to maintain a distraction which has already been created.

Ideally, adjustable implant 200 would be placed close to the instantaneous axis of rotation of spinal column 30 so that the reaction forces adjustable implant places on spinal column 30 are minimized.

For purposes of surgical implantation of adjustable implant 200 into a patient, the patient is preferably positioned on his side and placed in a flexed (tucked) position in order to distract the upper and lower vertebrae.

In a preferred procedure, a small incision is made on the midline of the spinous processes. The spinous processes are spread apart or distracted with a spreader. The incision is spread downwardly toward the table, and adjustable implant 200 is preferably inserted upwardly between the spinous processes 100 and 110 in a manner that maintains the distraction of spinous processes. The adjustable implant 200 is urged upwardly until guide 500 and at least part of wedging member 700 and/or 900 are visible on the other side of the spinous process. Once this is visible, the incision is spread upwardly away from the table and the retaining unit or second wing 2000 can be attached via screw 2130. Track 2110 can be used to space second wing 2000 relative to first wing 1800 (at least to the extent of allowable movement through slot 2110). After this had occurred, the incisions can be closed.

An alternative surgical approach requires that small incisions be made on either side of the space located between the spinous processes. The spinous processes are spread apart or distracted using a spreader placed through the upper incision. From the lower incision, adjustable implant 200 can be inserted upwardly between spinous processes 100 and 110 in a manner that urges the spinous processes apart. Adjustable implant 200 can be urged upwardly until guide 500 and at least part of wedging member 700 and/or 900 are visible through the second small incision in the patient's back. Once this is visible, second wing 2000 can be attached to guide 500 through screw 2130. After this has occurred, the incisions can be closed.

The advantage of the above two surgical procedures is that a surgeon is able to observe the entire operation, where he can look directly down onto the spinous processes as opposed to having to view the procedure from positions which are to the right and to the left of the spinous processes. Generally, the incision is as small as possible and the surgeon is working in a bloody and slippery environment. Thus, an implant that can be positioned directly in front of a surgeon is easier to insert and assemble than an implant which requires the surgeon to shift from side to side. Accordingly, a top-down approach, as an approach along a position to anterior line is preferred so that all aspects of the implantation procedure are fully visible to the surgeon at all times. This aides in the efficient location of (i) the adjustable implant 200 between the spinous processes, (ii) the retaining second wing 2000 in adjustable implant 200, and (iii) finally screw 2130 in adjustable implant 200.

In one embodiment the method can include implanting adjustable implant 200 between two spinous processes 100 and 110, expanding adjustable implant 200 a first amount, allowing spine 30 to creep or adjust to this first amount of distraction, and then expanding adjustable implant 200 a second amount, and then allowing a period of time spine 30 to creep or adjust to this new level of distraction. This process could be repeated until the desired amount of overall distraction has been accomplished. This stepped wise (and wait) distraction method can be used with insertion tools prior to the installation of adjustable implant 200. The tools can be used to obtain the desired distraction using a series of spinal distraction and spinal creep periods before first implanting adjustable implant 200.

One embodiment uses a dilator tool 4010 and a distractor tool 4020. The patient can be placed prone or lateral. A skin incision can be made over spinous processes 100 and 110 where the stenosis exists. The muscle will be moved off of the spinous process to the base bilaterally. If the facet joint is too large, the top can be removed to facilitate placement of adjustable implant 200 at the base of spinous process 110. The inter-spinous ligament is left intact. A small dilator 4010 can be placed through the inter-spinous ligament near the base. A second distracter 4020' is then used to open the space up to accommodate the smaller adjustable implant 200. Adjustable implant is then adjusted causing wedging members 700 and 900 to expand a desired amount in the direction of arrows 702 and 902. Adjustment is obtained by rotation of a control screw 1500 which rotates an adjustment screw or worm gear 1200. During this expansion process the surgeon can feel the inter-spinous ligament. Once taught, adjustable implant 200 can be allowed to sit and settle for a period of time (such as for five minutes). After this settling period of time, control screw 1500 can be tightened a bit more causing wedging members 700 and 900 to expand a bit more and ensure that the inter-spinous ligament remains taught. If adjustable implant 200 cannot be expanded to a point where there is the desired amount of stretching of the inter-spinous ligament, then a larger sized adjustable implant 200' can be used and adjusted accordingly. Adjustable implant allows the attachment of a second wing 2000 to prevent lateral dislodgment of adjustable implant from spinous processes 100 and 110. Preferably, the area is irrigated with antibiotics and saline and the muscle is injected with local anesthetic and the wound is closed.

FIGS. 16 through 18 show various steps in one embodiment of the method of implanting adjustable implant 200. FIG. 16 is a perspective view of a portion of a spinal column 30 where adjustable implant 200 is being inserted between a first spinous process 100 and a second spinous process 110 (guide 500 facilitates such insertion). FIG. 17 shows adjustable implant 200 being more fully inserted between a first spinous process 100 and a second spinous process 110 and second wing 2000 being attached. FIG. 18 shows adjustable implant 200 after first 700 and second 900 wedging members have been extended more fully (in the directions of arrows 702 and 902) pushing apart first spinous process 100 and second spinous process 110.

Additional Embodiments

Referring now to FIGS. 44-55, various adjustable implants are shown according to various exemplary embodiments. It should be understood that the implants shown and described with respect to FIGS. 44-55 may be used in combination with many of the features shown and described with respect to FIGS. 1-43 (e.g., lateral adjustment of wings, adjustable wedging members, etc.). All such combinations of features are understood to be within the scope of the present disclosure.

Figure 44:
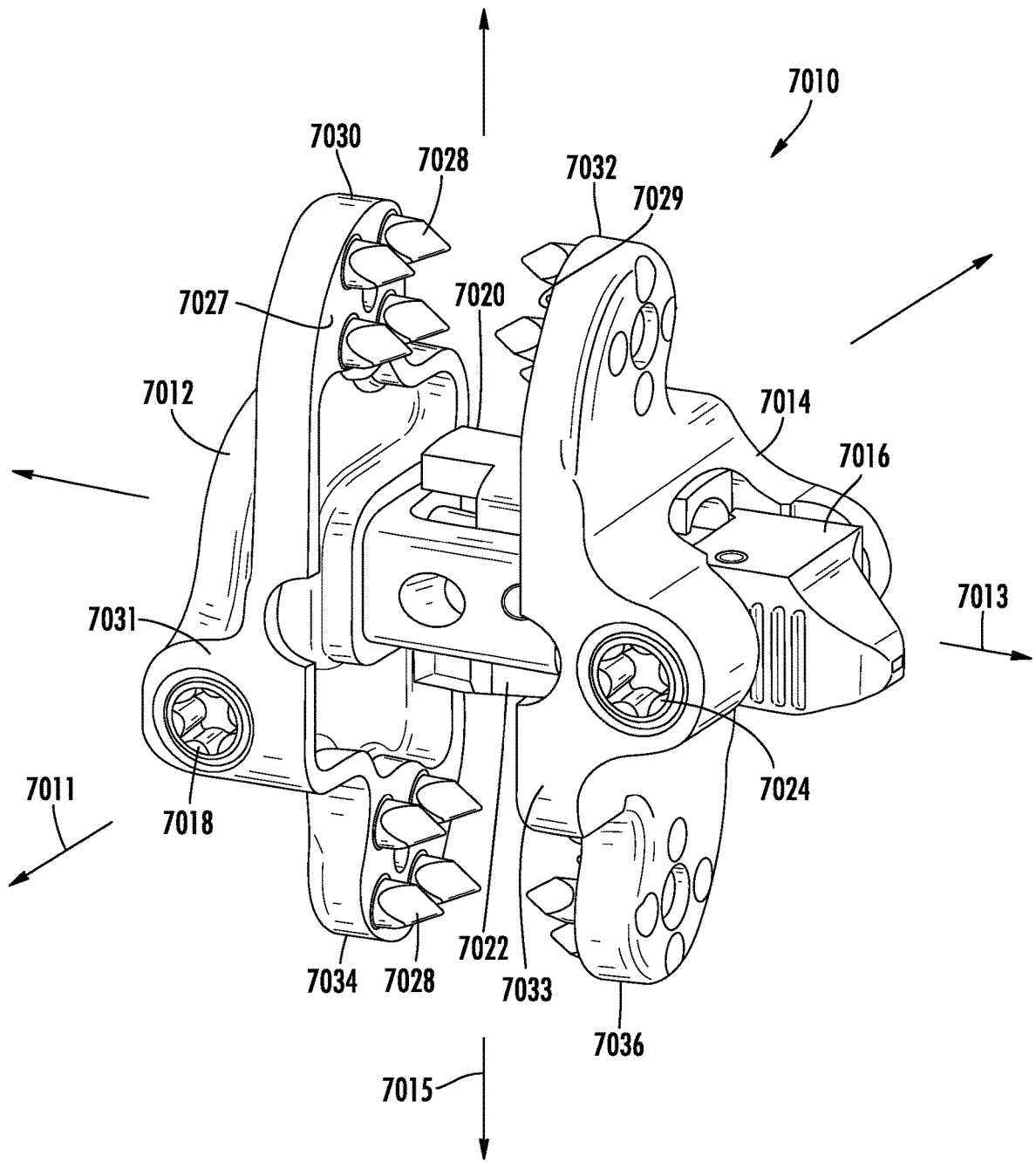
FIG. 44 is a perspective view of an implant according to another alternative embodiment.

Referring to FIGS. 44-46F, an adjustable spinal implant is shown according to an exemplary embodiment as implant 7010. Implant 7010 includes a first wing 7012 (e.g., a first lateral support, etc.), a second wing 7014 (e.g., a second lateral support, etc.), and a body portion 7016 (e.g., a guide, core, body, central portion, etc.) extending between first and second wings 7012, 7014. Body portion 7016 includes a sidewall extending from a first end to a second end. For purposes of better understanding the description of the embodiments herein, axes 7011, 7013, and 7015 are shown in FIG. 44 to illustrate the orientation of the implant once implanted in a patient relative to the anterior/posterior, superior/inferior, and right/left lateral directions. It should be noted that in some embodiments (see FIGS. 54-55) implant 7010 may be utilized in an orientation rotated 180 degrees relative to that shown in FIG. 44. As such, the relative positions of various components may change. All such variations are within the scope of the present disclosure.

In some embodiments, each of first and second wings 7012, 7014 includes an upper extension (e.g., one of upper extensions 7030, 7032) that extends away from the central portion (e.g., central portion 7031 or 7033) of the wing and includes a first offset portion 7039 offset to a first side (e.g., an anterior side) of the upper extension, and a lower extension (e.g., one of lower extensions 7034, 7036) that extends away from the central portion of the wing and includes a second offset portion 7041 offset to a second side of the lower portion. In one embodiment, first offset portion 7039 extends in a direction (e.g., anteriorly) generally opposite from second offset portion 7041.

According to an exemplary embodiment, first wing 7012 is coupled at or adjacent a first end of body portion 7016. First wing 7012 and body portion 7016 may be integrally formed, or alternatively may be coupled together using any suitable means (e.g., welding, adhesives, mechanical fasteners, press/snap fit, etc.). First wing 7012 includes a central portion 7031, an upper extension 7030 extending generally upward (e.g., superiorly) from central portion 7031, and a lower extension 7034 extending generally downward (e.g., inferiorly) from central portion 7031. Second wing 7014 comprises a central aperture 7017 permitting body portion 7016 to extend there through in an adjustable manner such that the lateral distance between first and second wings 7012, 7014 may be adjusted to fit a particular patient (e.g., in accordance with one or more spinous processes disposed between first and second wings 7012, 7014). Second wing 7014 includes a central portion 7033, an upper extension 7032 extending generally upward (e.g., superiorly) from central portion 7033, and a lower extension 7036 extending generally downward (e.g., inferiorly) from central portion 7033.

According to an exemplary embodiment, first wing 7012 is fixed relative to body portion 7016 and second wing 7014 is moveable along a gripping portion 7058 of body portion 7016. In one embodiment, the first and/or second wings 7012, 7014 at least partially encircle the body portion 7016. A positioning screw (e.g., a set screw, etc.) 7024 is received within a threaded bore 7070 of second wing 7014 and enables a physician to secure second wing 7014 in a desired lateral position relative to body portion 7016 and first wing 7012. Gripping portion 7058 may extend along all or a portion of the length of body portion 7016, and further may be disposed on one or more surfaces of body portion 7016. For example, while gripping portion 7058 is shown on a posterior surface, it may additionally and/or alternatively be provided on a superior, inferior, and or anterior surface of body portion 7058. The length of body portion 7016 may be such so as to allow implant 7010 to accommodate a wide range of sizes of spinous processes of different patients.

According to an exemplary embodiment, body portion 7016 includes one or more expandable portions, shown as wedging members 7020, 7022. Wedging members 7020, 7022 are configured to provide superior/inferior adjustment capabilities to implant 7010 to accommodate various amounts of desired distraction. In one embodiment a least one of wedging member 7020, 7022 are movable relative to the sidewall of the body portion 7016 and includes an external wedging surface configured to engage bone. A control screw 7018 is received within a bore 7068 in central body 7016 and a control screw pin 7046 extends adjacent a recess 7048 in control screw 7018 to retain control screw 7018 in place. Control screw 7018 engages a gear 7038 which is in turn coupled and keyed to a rotatable splined shaft 7040. Splined shaft 7040 is retained in place by a shaft pin 7062 received in a recess 7064. The splines on shaft 7040 engage the teeth formed on panels 7042, 7044 of wedging members 7020, 7022 to control the relative positions of wedging members 7020, 7022 and the amount of distraction provided by implant 7010. As such, rotation of control screw 7018 results in an increasing/decreasing amount of distraction between wedging members 7020, 7022. Wedging members 7020, 7022 are held in place, and the total amount of distraction available is limited by, wedging member pins or retention pins 7050, 7052 being received within recesses or channels 7054, 7056 of wedging members 7020, 7022. In some embodiments, the channels 7054, 7056 are elongated in the direction of movement of the wedging members 7020, 7022 and the wedging member pins 7050, 7052 are coupled to the sidewall and received in the channels 7054, 7056 such that the wedging member pins 7050, 7052 limit a maximum expansion of the wedging members 7020, 7022. Control screw 7018 permits a physician to insert implant 7010 with wedging members in a lowered position and subsequently move wedging members 7020, 7022 to a desired position via rotation of control screw 7018.

According to an exemplary embodiment, first and second wings 7012, 7014 include inward facing surfaces 7027, 7029. Surfaces 7027, 7029 are configured to engage and/or be positioned adjacent to opposite sides of first and second spinous processes. A recess 7026 may be formed in one or both of surfaces 7027, 7029 to provide a space to receive bone growth material (e.g., a flowable bone growth composite, etc.). In some embodiments, recesses 7026 have a generally uniform depth relative to surfaces 7027, 7029 and cover a substantial portion of the inner surfaces of central portions 7031, 7033 of wings 7012, 7014. In some embodiments, recess 7026 is a single recess that extends both above and below body portion 7016 (e.g., in both a superior and inferior direction). In some embodiments, recess 7026 may be provided on both of wings 7012, 7014, while in other embodiments, recess 7026 may be provided on only one of wings 7012, 7014. In yet further embodiments, the recesses on wings 7012, 7014 may be mirror images of one another, forming like-sized cavities relative to the outer surfaces of the spinous processes.

According to an exemplary embodiment, first and second wings 7012, 7014 and/or body portion 7016 may include one or more apertures extending all or a portion of the way therethrough to receive bone growth material (e.g., flowable bone composite, etc.) and to promote bone growth in and around implant 7010. For example, first wing 7012 may include upper and lower apertures 7074, 7078 extending through upper and lower extensions 7030, 7034, respectively. Similarly, second wing 7014 may include upper and lower apertures 7076, 7080 extending through upper and lower extensions 7032, 7036, respectively. Furthermore, central portion 7016 may include an aperture 7072 extending through all or a portion thereof. According to various alternative embodiments, the number, position, size, and configuration of the various apertures provided on first and second wings 7012, 7014 and body portion 7016 may be varied to suit a particular patient I implant and to maximize bone growth in and around implant 7010.

Figure 45:
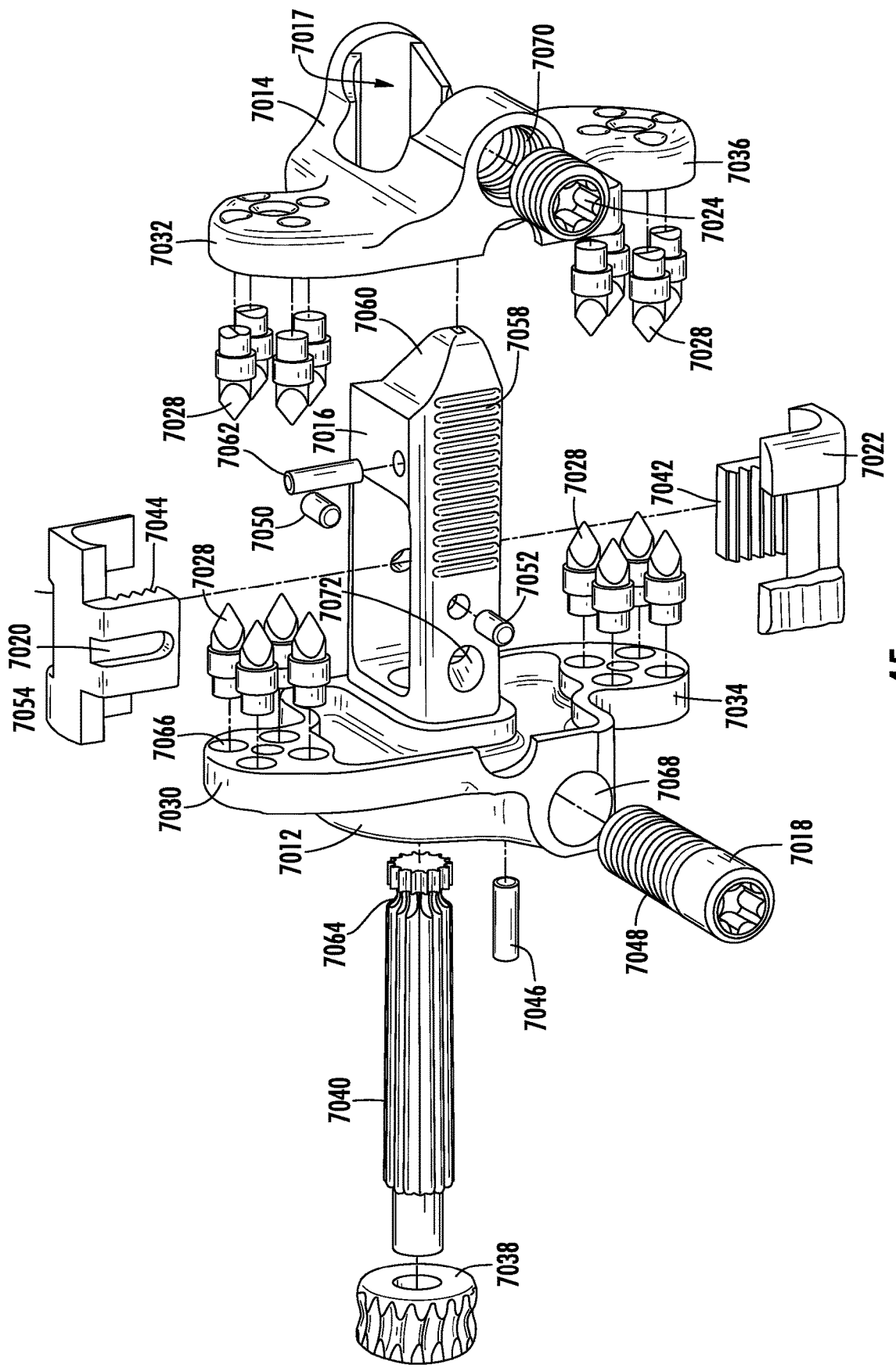
FIG. 45 is an exploded perspective view of the implant of FIG. 44 according to an exemplary embodiment.
Figure 46D:
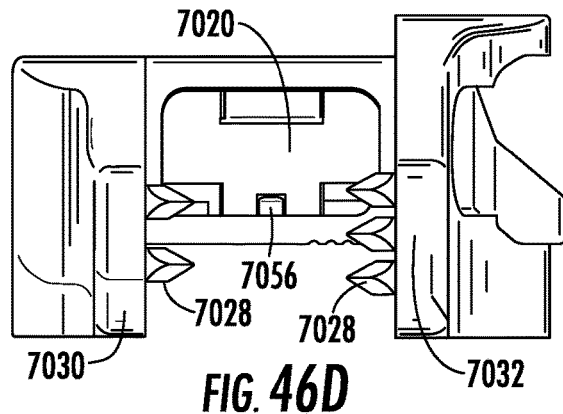
FIG. 46D is a top view of the implant of FIG. 44 according to an exemplary embodiment.
Figures 46A, 46B, 46C:
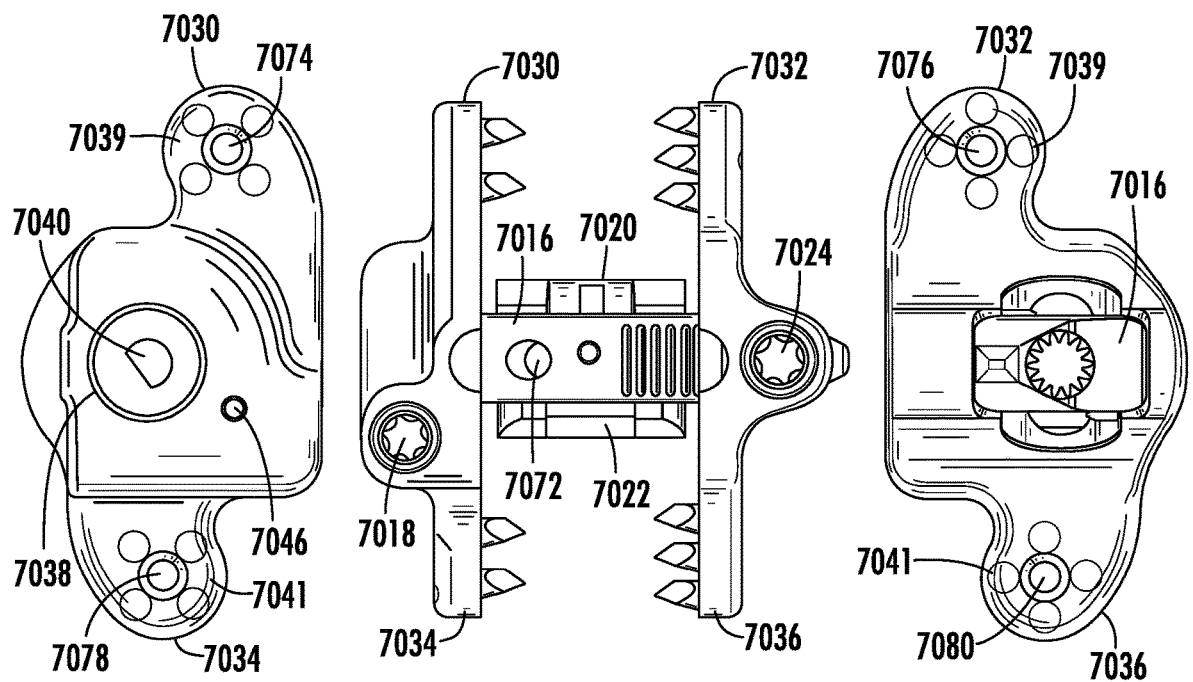
FIG. 46A is a front view of the implant of FIG. 44 according to an exemplary embodiment.
FIG. 46B is a left side view of the implant of FIG. 44 according to an exemplary embodiment.
FIG. 46C is a right side view of the implant of FIG. 44 according to an exemplary embodiment.
Figure 46E:
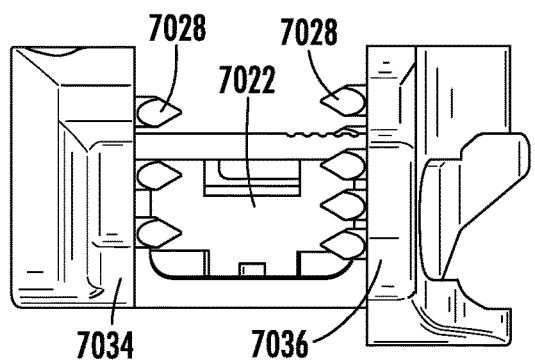
FIG. 46E is a bottom view of the implant of FIG. 44 according to an exemplary embodiment.
Figure 46F:
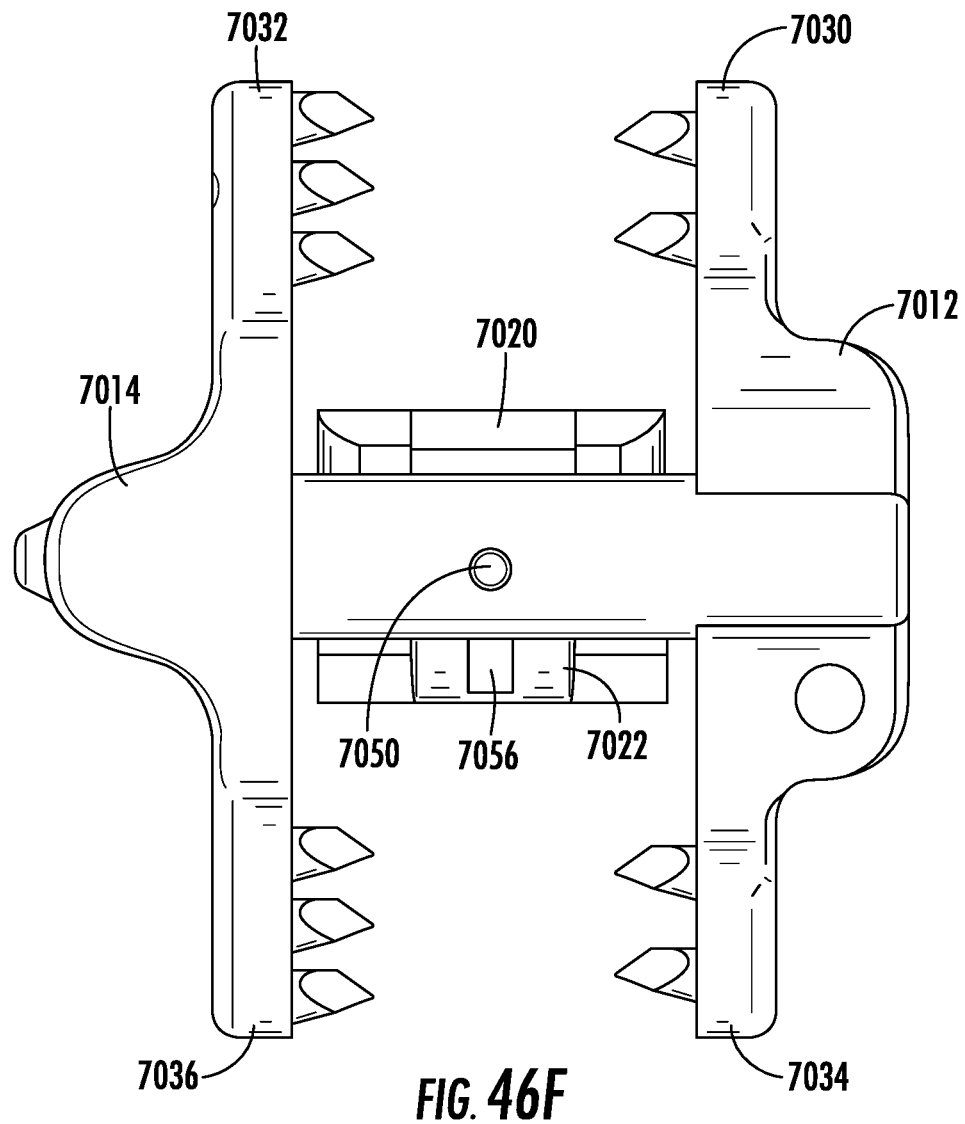
FIG. 46F is a rear view of the implant of FIG. 44 according to an exemplary embodiment.

According to some embodiments, upper extensions 7030, 7032 and lower extensions 7034, 7036 may be curved in shape, for example, to form curved, wave-like extensions extending superiorly/inferiorly and anteriorly/posteriorly away from central portions 7031, 7033 of wings 7012, 7014. For example, as shown in FIGS. 46B-C, upper extensions 7030, 7032 may extend from a posterior side of central portions 7031, 7031 and extend superiorly and anteriorly from central portions 7031, 7033, and lower extensions 7034, 7036 may extend from an anterior side of central portions 7031, 7033 and extend inferiorly and posteriorly from central portions 7031, 7033. In an alternative embodiment, implant 7010 may installed in a position rotated 180 degrees from that shown in FIGS. 44-46F (see FIGS. 54-55) such that the extensions 7034, 7036 would extend away superiorly and posteriorly from the anterior sides of central portions 7031, 7033, and extensions 7030, 7032 would extend away inferiorly and anteriorly from the posterior sides of central portions 7031, 7033.

In some embodiments, the relative positions and curved profile of the extensions may provide a more stable configuration for implant 7010 relative to more conventional device configurations. Furthermore, the upper and lower extensions are configured such that should multiple implants may be required along portions of the spine, adjacent implants tend to nest together in a complimentary fashion due to the geometry of the extensions. As such, wings 7012, 7014 are able to "grab" lower onto the spinous processes while permitting the device to maintain a generally posterior, or proud, position between adjacent spinous processes.

According to an exemplary embodiment, one or more of extensions 7030, 7032, 7034, 7036 include projections 7028 (e.g., protrusions, spikes, pointed members, etc.) extending inward from inward surfaces 7027, 7029. For example, as shown in FIGS. 44-45, each extension includes four projections 7028 extending inward therefrom. Projections 7028 may be coupled to wings 7012, 7014 using any suitable means, including welding, press-fit, snap-fit, mechanical fasteners, a threaded engagement, etc. In one embodiment the four projections on each extension are formed so as to be offset relative to the four projections on the co-facing surface of the other wing. For example, projections 7028 provided on extension 7030 may form a generally square shape. Similarly, projections 7028 provided on extension 7032 may form a generally square shape that is rotated (e.g., 90 degrees) relative to the square shape formed by projections 7028 on extension 7030. As such projections 7028 will not be provided directly opposite from one another, which may improve the gripping effect of the extensions.

According to various alternative embodiments, other configurations of projections 7028 may be utilized. For example, in some embodiments, more or fewer than four projections (e.g., 2, 3, 5, etc.) may be provided on the inner surface of each extension. Furthermore, the projections may vary in length, diameter, etc. Further yet, projections 7028 may be omitted on one or more of the extensions. Other variations in the size, placement, etc. of projections 7028 may be made according to various other embodiments.

Referring further to FIGS. 44-45, body portion 7016 may include a curved or bull-nosed shaped portion shown as nose 7060 extending from one end thereof. According to one embodiment, nose 7060 provides a portion of reduced cross-section that may gradually increase in cross-section. In one embodiment, implant 7010 is configured to be inserted such that nose 7060 is inserted into the patient first, and then implant 7010 is rotated approximately 90 degrees into its final position (see, e.g., FIGS. 54-55). In some embodiments, implant 7010 is inserted without second wing 7014 attached (see FIG. 54), and second wing 7014 is then slid onto body portion 7016 once implant 7010 is in position (see FIG. 55).

Figure 47:
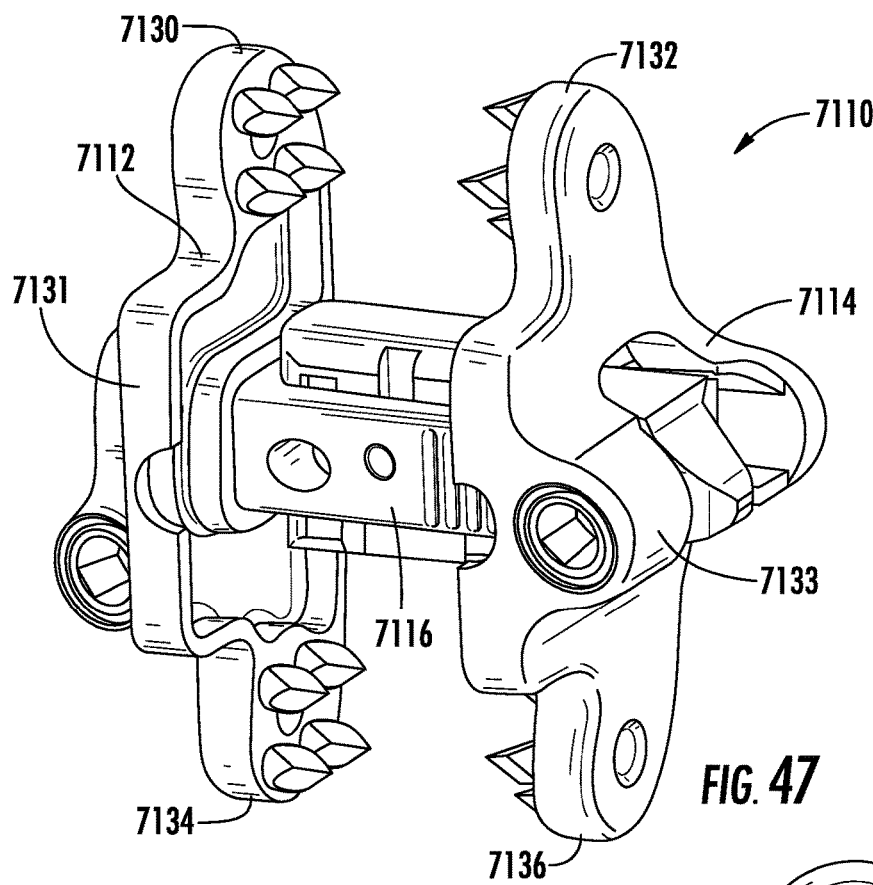
FIG. 47 is a perspective view of an implant according to another alternative embodiment.
Figure 48:
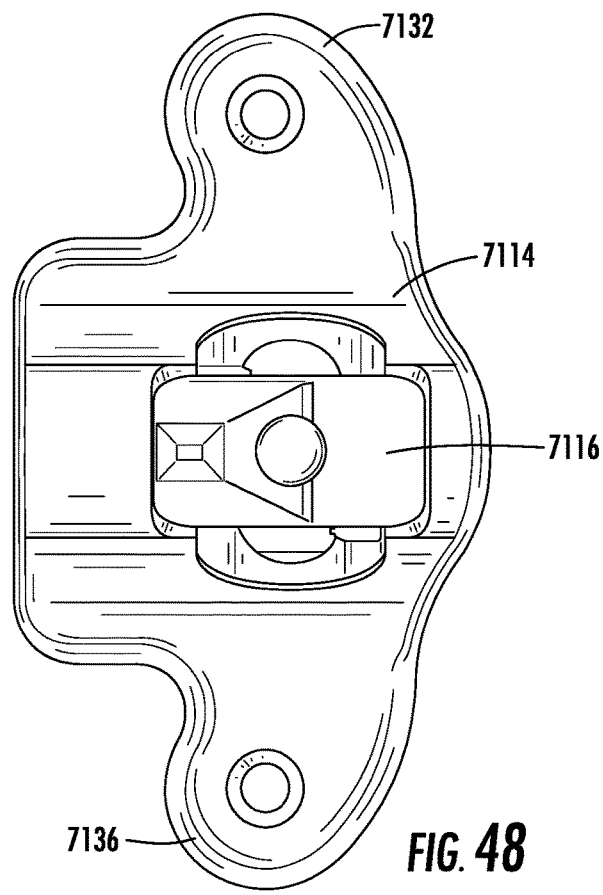
FIG. 48 is a side view of the implant of FIG. 47 according to an exemplary embodiment.

Referring now to FIGS. 47-48, an implant 7110 is shown according to an alternative embodiment. Implant 7110 is generally similar to implant 7010 in construction and function except for the location and shape of upper extensions 7130, 7132. As shown in FIGS. 47-48, implant 7110 includes a first wing 7112, a second wing 7114, and a body portion 7116 extending therebetween. First wing 7112 includes an upper extension 7130 and a lower extension 7134 extending from a central portion 7131. Second wing 7114 includes an upper extension 7132 and a lower extension 7136 extending from a central portion 7133. Upper extensions 7130, 7132 extend superiorly and superiorly from central portions 7131, 7133, and lower extensions 7134, 7136 extend inferiorly and superiorly from central portions 7131, 7133. As such, both upper extensions 7130, 7132 and lower extensions 7134, 7136 extend at least partially superiorly once implant 7110 is installed within a patient.

In some embodiments, implant 7110 is intended to contour to the anatomy of the spone between the L5 spinous process and the spinous tubercle of the sacrum. The sacral profile of implant 7110 (e.g., the "boat" shaped profile shown in FIG. 48) permits the spikes to grab both processes as anterior as possible.

Figure 49:
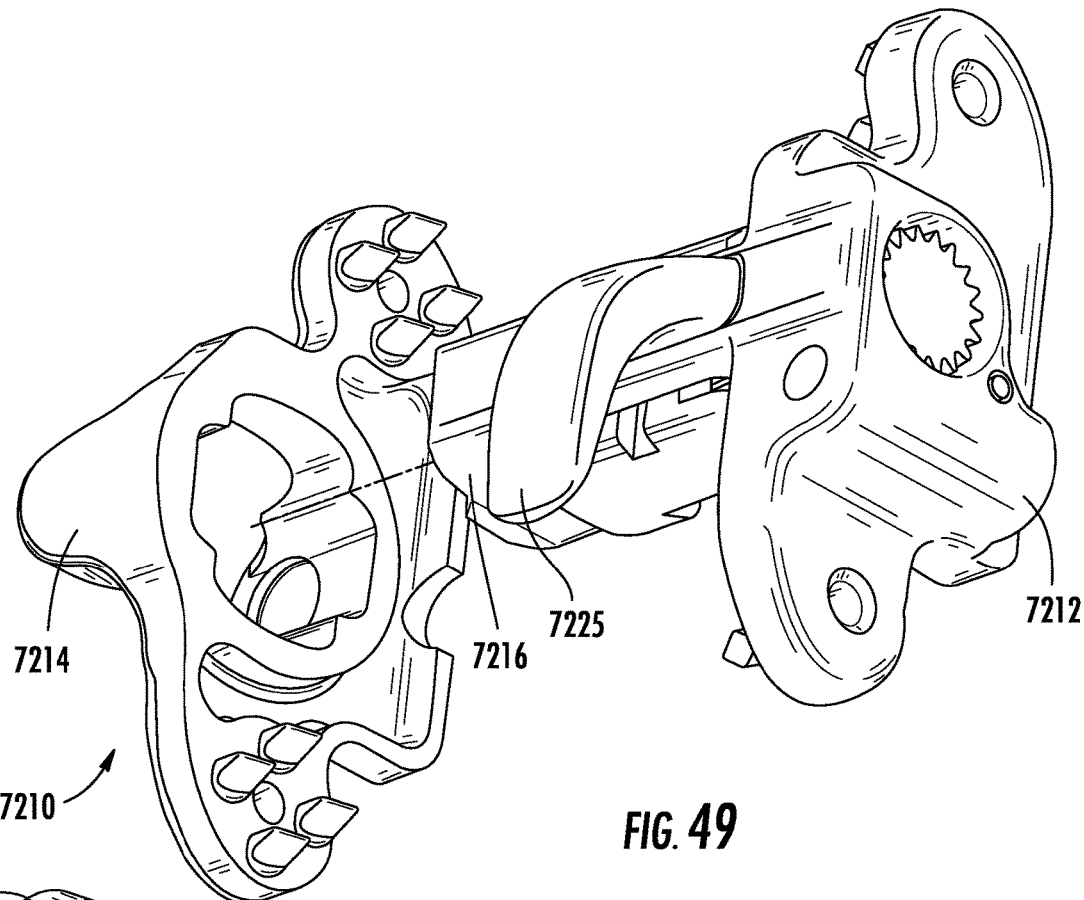
FIG. 49 is a partially exploded rear view of an implant according to another alternative embodiment.
Figure 50:
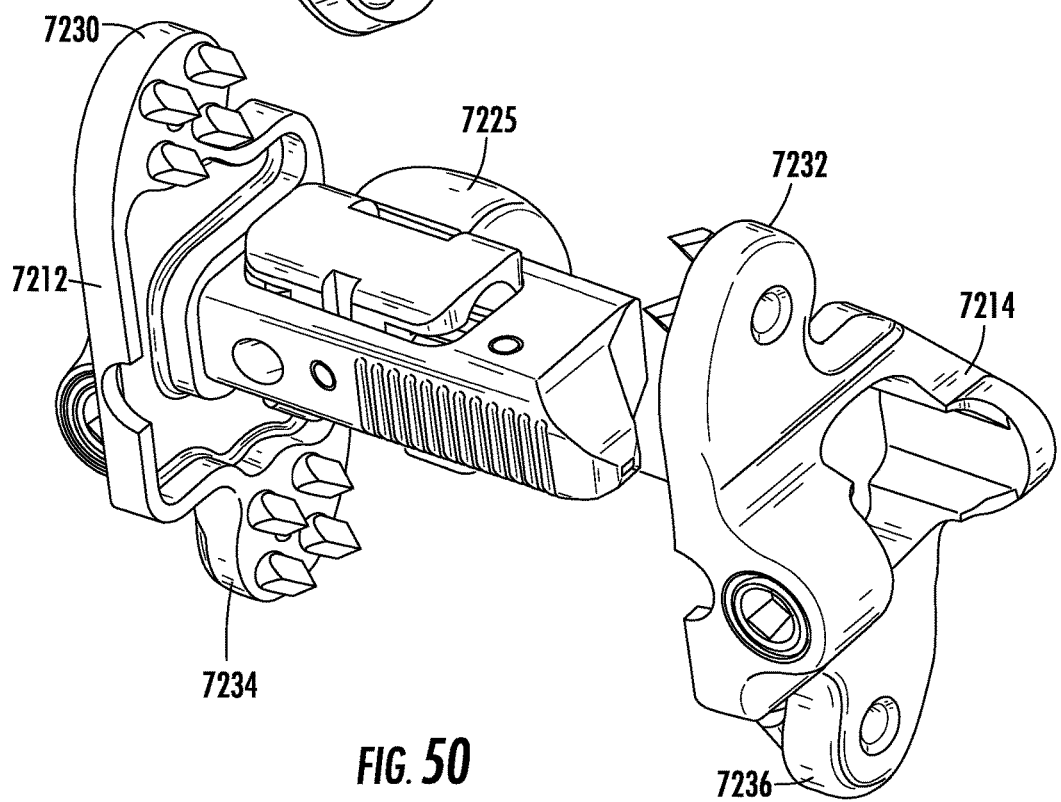
FIG. 50 is a partially exploded front perspective view of the implant of FIG. 49 according to an exemplary embodiment.
Figure 51:
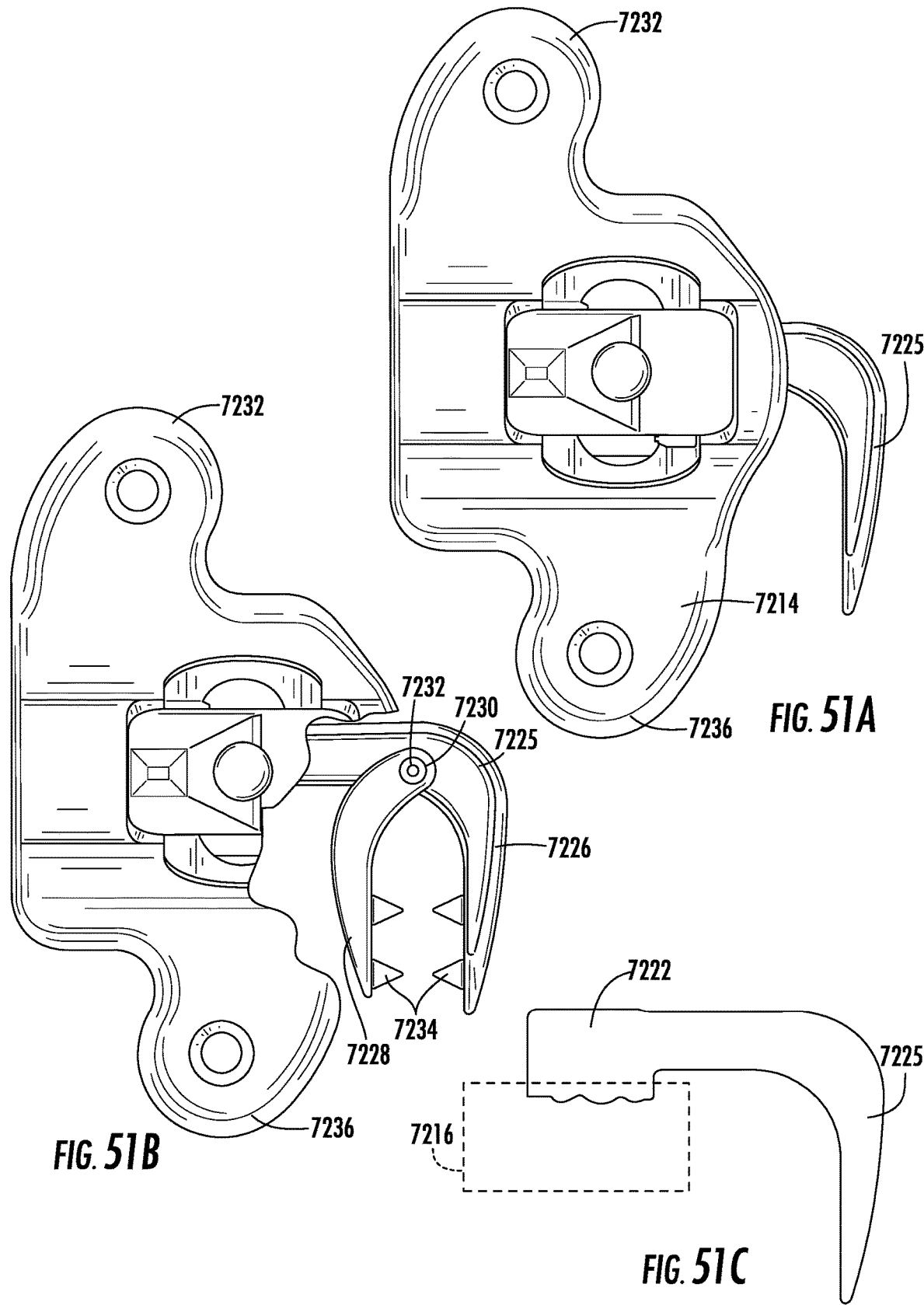
FIG. 51A is a side view of the implant of FIG. 49 according to an exemplary embodiment.
FIG. 51B is a side view of a portion of an implant according to an exemplary embodiment.
FIG. 51C is a side view of a portion of an implant according to an exemplary embodiment.

Referring now to FIGS. 49-51, an implant 7210 is shown according to another alternative embodiment. Implant 7210 is generally similar to implant 7010 in construction and function except that implant 7210 further includes a hook portion 7225 (e.g., a laminar hook, etc.). As shown in FIGS. 49-51, hook portion 7225 extends from body portion 7216 in an anterior and inferior direction. In one embodiment, hook portion 7225 is an L-shaped member that extends anteriorly from body portion 7216 and then turns approximately 90 degrees downward to extend generally inferiorly. The hook portion 7225 may include a first end coupled to the body portion 7216 and a second end opposite the first end of the hook portion 7225. In one embodiment, a first hook portion extends from the body portion 7216 in a first direction and a second hook portion extends from the first hook portion in a second direction different from the first direction. The hook portion 7225 may include an L-shaped portion defined by the first hook portion and the second hook portion, such that the first hook portion and the second hook portion form approximately a 90 degree angle. According to some embodiments, the thickness of hook portion 7225 decreases from the portion coupled to body portion 7216 toward the opposite end of hook portion 7225. In one embodiment, the first hook portion is thicker than the second hook portion Hook portion is configured to provide further stability in positioning and maintaining implant 7210. For example, if the patient's anatomy does not provide for a large enough tubercle on the sacrum for spikes to attach, hook portion 7225 may be utilized to "grab" the sacral canal for attachment. In some embodiments, hook portion 7225 may be used on any processes in the lumbar region, and can serve as an option for any missing or degenerative spinous process.

In some embodiments, hook portion 7225 may be integrally formed with body portion 7216. In other embodiments, hook portion may be a separately formed component of implant 7210 that may be fastened to implant 7210 using any suitable means (e.g., welding, snap/interference fit, mechanical fasteners, etc.). In yet further embodiments, hook portion 7225 may be selectively coupled to and removed from body portion 7216 to use hook portion 7225 only when desired or appropriate. The shape, size, location, and configuration of hook portion 7225 may be varied to suit a particular patient and/or installation.

Referring to FIG. 51B, in some embodiments, hook portion 7225 may comprise a first jaw or clamp member 7226 and a second jaw or clamp member 7228 coupled together via a joint or pivot 7230. In various embodiments, one or both of clamp members 7226, 7228 may articulate or pivot about joint 7230. In one embodiment, one or both of claim members 7226, 7228 may be biased by a spring member 7232 toward the other member to provide improved clamping force (e.g., on the sacral canal). According to an exemplary embodiment, one or both of clamping members 7226, 7228 may include spikes or projections 7234 to further improve the retention capabilities of hook portion 7225. In one embodiment, clamp member 7228 and hook portion 7225 (e.g., clamp member 7226) are configured such that clamp member 7228 includes at least one first projection on an inside surface of clamp member 7228 and clamp member 7226 includes at least one second projection on an inside surface of clamp member 7226. Hook portion 7225 may be used to clamp the lamina along all of the lumbar region of the spine (e.g., not being limited to use in the L5-S1 region of the spine. In one embodiment, clamp member 7228 is a movable clamp member and is coupled to or part of the hook portion 7225 and includes a first end and a second end opposite the first end of the clamp member 7228. Movable clamp member 7228 may be rotatably coupled to the hook portion 7225 such that a distance between a second end of the hook portion 7225 and the second end of the movable clamp member 7228 may be adjusted by rotating the movable clamp member 7228.

Referring to FIG. 51C, in some embodiments, hook portion 7225 may be coupled to one of upper or lower wedging members 7220, 7222, to provide superior/inferior adjustment features for hook portion 7225. As such, hook portion 7225 may in some embodiments be movable superiorly/inferiorly relative to body portion 7216. Hook portion 7225 may be integrally formed with one of wedging members 7220, 7222, or optionally may be coupled to wedging members 7220, 7222 using any suitable coupling/fastening technique.

Figure 52:
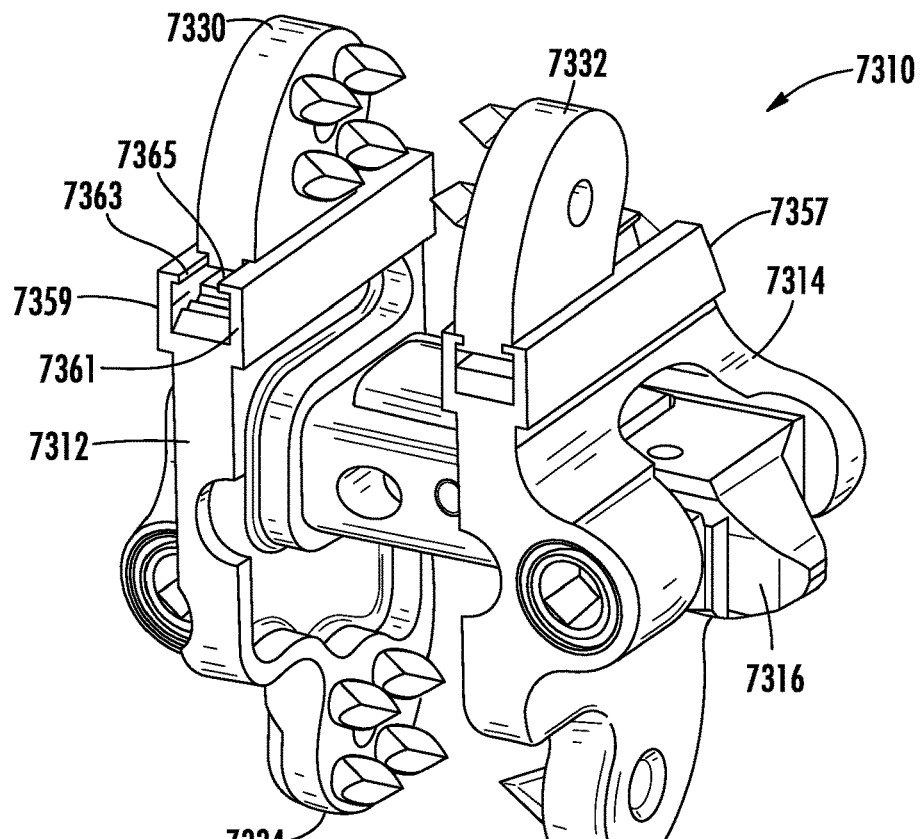
FIG. 52 is a perspective view of an implant according to another alternative embodiment.
Figure 53:
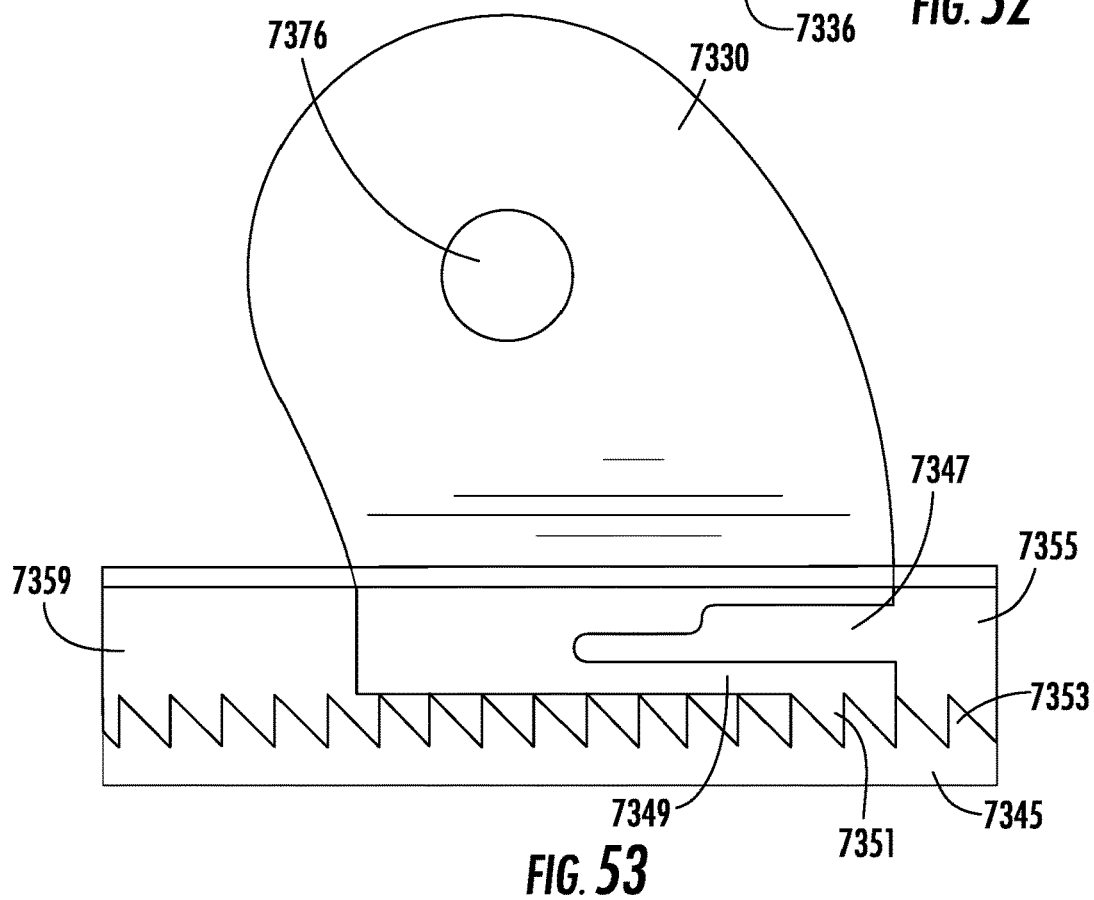
FIG. 53 is a schematic cross-sectional view of a portion of the implant of FIG. 52 according to an exemplary embodiment.

Referring now to FIGS. 52-53, an implant 7310 is shown according to yet another alternative embodiment. Implant 7310 is similar to implant 7010 in construction and function except that implant 7310 includes adjustable extensions 7330, 7332. As shown in FIGS. 52-53, implant 7310 includes a first wing 7312, and second wing 7314, and a body portion 7316. First wing 7312 includes an upper extension 7330 and a lower extension 7334 extending from a central portion 7331 of first wing 7312. Similarly, second wing 7314 includes an upper extension 7332 and a lower extension 7336 extending from a central portion 7333 of second wing 7314.

According to an exemplary embodiment, upper extensions 7330, 7332 of first and second wings 7312, 7314 are adjustable anteriorly/posteriorly relative to central portions 7331, 7333. For example, upper extensions 7330, 7332 may be adjustable such that in a posterior position, extensions 7330, 7332 are generally flush with the posterior surfaces of first and second wings 7312, 7314, and in an anterior position, extensions 7330, 7332 are generally flush with the anterior surfaces of first and second wings 7312, 7314. Further, extensions 7330, 7332 may be adjusted to any of a number of positions between the posterior and anterior positions. Further yet, extensions 7330, 7332 may be adjustable between discreet positions, or alternatively, may be adjustable between an infinite number of selectable positions between the posterior and anterior positions.

Any suitable adjustment mechanism may be utilized to secure extensions 7330, 7332 in a desired position. Referring to FIG. 53, an adjustment mechanism for adjusting extension 7330 is shown according to an exemplary embodiment, it being understood that a similar adjustment mechanism may be used in connection with extension 7332. As shown in FIG. 53, a lower portion 7349 of extension 7330 is configured to travel within a channel 7355 formed in central portion 7331. In one embodiment, channel 7355 is formed by a pair of upstanding sidewalls 7359, 7361 that extend upward from a channel bottom 7345 and include inward extending flanges 7363, 7365 configured to be received in corresponding grooves or recesses in extension 7330 and retain extension 7330 within channel 7355.

In some embodiments, lower portion 7349 of extension 7330 includes one or more teeth 7351 configured to selectively engage corresponding teeth 7353 provided on channel bottom 7345. Teeth 7351, 7353 may be provided with corresponding profiles the permit movement of extension 7330 relative to central portion 7331, yet require some force to be applied in order to move the position of extension 7330. In one embodiment, a recess 7347 is formed in extension 7330 such that lower portion 7349 of extension 7330 is flexible I compliant, and further such that teeth 7351, 7353 may be disengaged from one another upon application of a force tending to move lower portion 7349 along channel bottom 7345. In some embodiments, lower portion 7349 and recess 7347 form a compliant arm having a pair of teeth 7351 extending from the end thereof. According to other embodiments, other locations, sizes, shapes, and numbers of teeth 7351 may be utilized.

In one embodiment, extension 7330 is configured to be adjustable in both a posterior and an anterior direction. In other embodiments, extension 7330 is moveable in only one of an anterior and a posterior direction. Further, extension 7330 may be adjustable after implant 7310 has been implanted within a patient.

It should be noted that while FIGS. 52-53 shown upper extensions 7330, 7332 as being adjustable extensions, more or fewer of the extensions of implant 7310 may be made adjustable in a similar fashion. For example, in some embodiments, all of the extensions may be adjustable, or only the extensions on a single wing, etc. Furthermore, the shape of the adjustable extensions may take any of the shapes discussed herein. Further yet, apertures such as aperture 7376 may be provided in extensions such as adjustable extension 7330 to promote bone growth in and around implant 7310.

Figure 54:
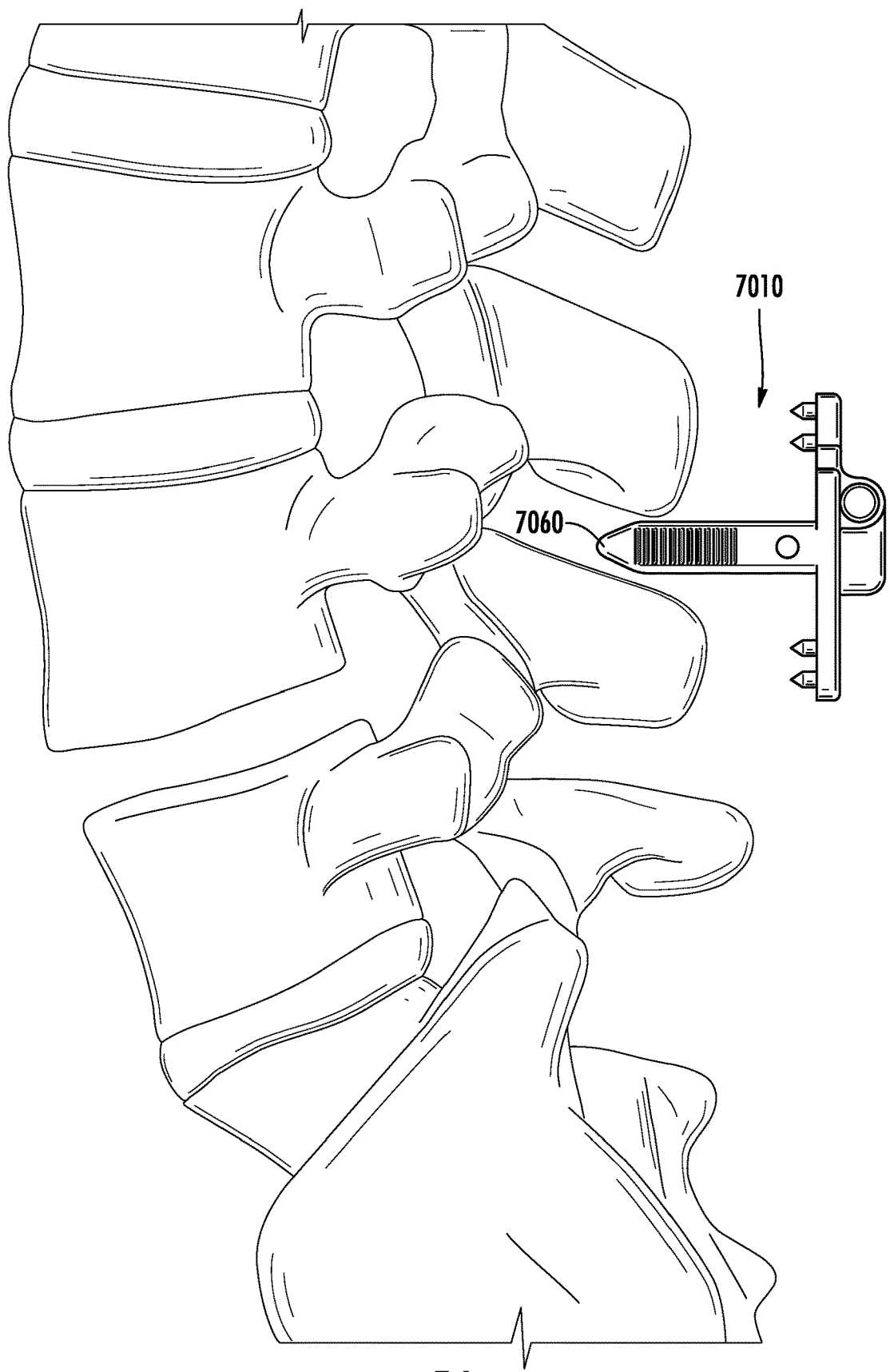
FIG. 54 is a perspective view of an implant being inserted into a spine according to an exemplary embodiment.
Figure 55:
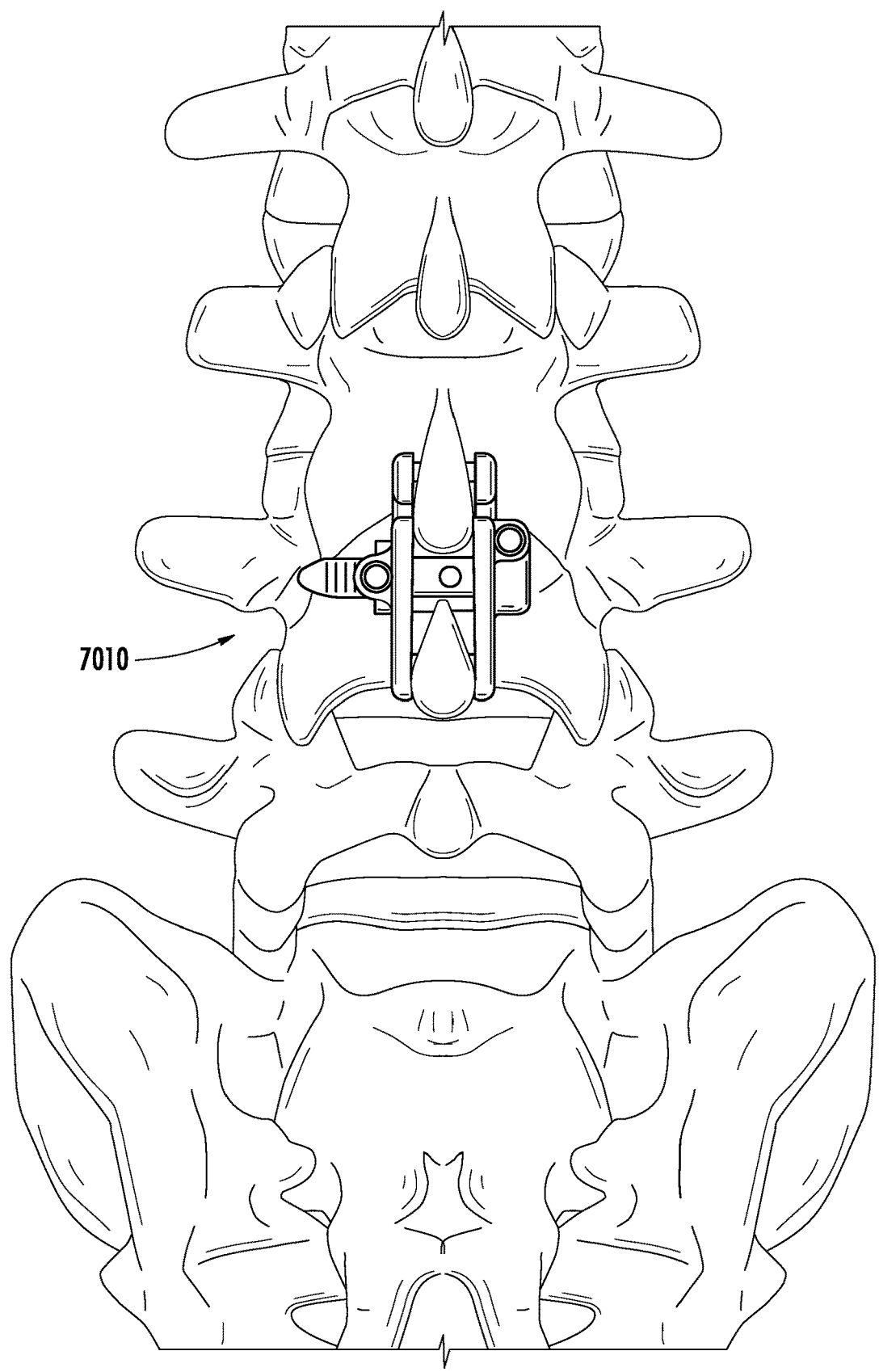
FIG. 55 is a front view of an implant positioned within a spine according to an exemplary embodiment.

Referring to FIGS. 54-55, implant 7010 is shown being inserted into a patient (see FIG. 54) and in the implanted state (FIG. 55). As shown in FIG. 54, implant 7010 may be inserted with nose 7060 pointed toward the implantation site and with second wing 7014 removed. After insertion, implant 7010 may be rotated 90 degrees, second wing 7014 attached, and implant 7010 secured into final position. A similar implantation technique may be utilized with any of the alternative embodiments discussed herein. It should be noted that implant 7010 as shown in FIGS. 54-55 is rotated 180 degrees relative to implant 7010 shown in FIG. 44 and other FIGURES herein. The relative orientation of the implant within the patient may be selected based on the needs and characteristics of the individual patient.

The implants shown in and described with respect to FIGS. 44-53 may provide various advantages over conventional implants. The projections extending from the inner surfaces of the wings may provide greater gripping forces for the wings and provide a more stable implant. The recesses and apertures provided in the wings and/or body portion can accommodate flowable bone composite material and promote bone growth in and about the implant. Further, the bull-nosed body portion and wave-shaped wings facilitate insertion of the implant and provide lower "gripping features" of the wings relative to the spinous processes while maintaining a posterior position for the implant. Further yet, the expandable wedging members provide for an adjustable amount of distraction.

INDUSTRIAL APPLICABILITY

From the above, it is evident that the embodiments can be used to relieve pain caused by spinal stenosis in the form of such as that caused by central canal stenosis or foraminal (lateral) stenosis. Various embodiments have the ability to flatten the natural curvature of the spine and open the neural foramen and the spacing between adjacent vertebra to relieve problems associated with the above-mentioned lateral and central stenosis. Additionally, various embodiments can be used to relieve pain associated with facet arthropathy. Various embodiment can be implanted with surgery that is minimally invasive and can be used on an outpatient basis.

All measurements disclosed herein are at standard temperature and pressure, at sea level on Earth, unless indicated otherwise. All materials used or intended to be used in a human being are biocompatible, unless indicated otherwise.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims

What is claimed is:

1. An adjustable implant comprising:
   a body portion including:
      a first end;
      a second end including a bull nose; and
      a sidewall extending from the first end to the second end;
   a hook coupled to the body portion, the hook including:
      a first hook portion extending from the body portion in a first direction; and
      a second hook portion extending from the first hook portion in a second direction different from the first direction, wherein the hook further includes a movable clamp member having a first end and a second end opposite the first end;
   a first wing coupled to the first end of the body portion; and
   a second wing coupled to the body portion such that a distance between the first wing and the second wing is adjustable by a user, wherein the first and second wings include inward facing surfaces configured to be positioned adjacent portions of bone of a patient;
   wherein the hook includes an L-shaped portion defined by the first hook portion and the second hook portion, such that the first hook portion and the second hook portion form approximately a 90 degree angle.

2. The adjustable implant of claim 1, wherein the first hook portion is thicker than the second hook portion.

3. The adjustable implant of claim 2, wherein the hook is integrally formed with the body portion.

4. The adjustable implant of claim 1, wherein the first end of the movable clamp member is rotatably coupled to the first hook portion, such that a distance between the second hook portion and the second end of the movable clamp member may be adjusted by rotating the movable clamp member.

5. The adjustable implant of claim 4, wherein the movable clamp member includes at least one first projection on an inside surface of the movable clamp member and the second hook portion includes at least one second projection on an inside surface of the second hook portion, wherein the inside surface of the movable clamp member faces the inside surface of the second hook portion.

6. The adjustable implant of claim 4, wherein the movable clamp member is biased towards the second hook portion.

7. An adjustable implant comprising:
   a body portion including:
      a sidewall extending from a first end of the body portion to a second end of the body portion;
      a first wedging member movable relative to the sidewall and including a first external wedging member surface configured to engage bone, a first panel extending from a first side of the first external wedging member surface and defining a channel elongated in a direction of movement of the first wedging member, and a pair of second panels extending from a second side of the first external wedging member surface and
      a second wedging member movable relative to the sidewall and including a second external wedging member surface configured to engage bone, a third panel extending from a first side of the second external wedging member surface, and a pair of fourth panels extending from a second side of the second external wedging member surface;
      a retention pin coupled to the sidewall and received in the channel of the first panel to limit a maximum expansion of the first wedging member;
   a first wing coupled to the first end of the body portion, wherein the first wing at least partially encircles the body portion; and
   a second wing adjustably coupled to the body portion, wherein the second wing at least partially encircles the body portion, such that a distance between the first wing and the second wing is adjustable by a user;
   wherein the first and second wedging members are movable independent from the first and second wings, and wherein when the first wedging member and the second wedging member are in a collapsed position, the first panel is positioned between and adjacent the pair of fourth panels, and the third panel is positioned between and adjacent the pair of second panels wherein the first panel engages the pair of fourth panels and the third panel engages the pair of second panels to maintain an alignment of the first wedging member and the second wedging member within the sidewall as the first wedging member moves between the collapsed position and a position of the maximum expansion.

8. The adjustable implant of claim 7, further comprising a hook portion coupled to the body portion, wherein the hook portion includes at least one bend, and wherein the hook portion includes a first end coupled to the body portion and a second end opposite the first end of the hook portion.

9. The adjustable implant of claim 8, wherein the first end of the hook portion is selectively coupled to the body portion.

10. The adjustable implant of claim 8, wherein the hook portion is integrally formed with one of the first wedging member and the second wedging member.

11. The adjustable implant of claim 8, further comprising a movable clamp member coupled to the hook portion, wherein the movable clamp member includes a first end and a second end opposite the first end of the movable clamp member.

12. The adjustable implant of claim 11, wherein the first end of the movable clamp member is rotatably coupled to the hook portion, such that a distance between the second end of the hook portion and the second end of the movable clamp member may be adjusted by rotating the movable clamp member.

13. The adjustable implant of claim 12, wherein the movable clamp member includes at least one first projection on an inside surface of the movable clamp member and the hook portion includes at least one second projection on an inside surface of the hook portion, wherein the inside surface of the movable clamp member faces the inside surface of the hook portion.

14. The adjustable implant of claim 13, wherein the movable clamp member is biased towards the second end of the hook portion.

15. An adjustable implant comprising:
a body portion including:
a first end;
a second end, including a bull nose portion;
a sidewall extending from the first end to the second end;
a first wedging member movable relative to the sidewall and including a first external wedging member surface configured to engage bone, a first panel extending from a first side of the first external wedging member surface, and a pair of second panels extending from a second side of the first external wedging member surface, the first panel including a channel elongated in a direction of movement of the wedging member;
a second wedging member movable relative to the sidewall and including a second external wedging member surface configured to engage bone, a third panel extending from a first side of the second external wedging member surface, and a pair of fourth panels extending from a second side of the second external wedging member surface, wherein exterior surfaces of the first panel engage interior surfaces of the pair of fourth panels, and exterior surfaces of the third panel engage interior surfaces of the pair of second panels; and
a retention pin coupled to the sidewall and received in the channel such that the retention pin limits maximum expansion of the first wedging member;
a first wing coupled to the first end of the body portion;
a second wing adjustably coupled to the body portion, wherein the first and second wings include inward facing surfaces configured to be positioned adjacent portions of bone of a patient;
wherein the first and second wedging members move independent from the first and second wings.

16. The adjustable implant of claim 15, wherein a distance between the first wing and the second wing is adjustable by a user.

17. The adjustable implant of claim 16 further comprising a hook portion coupled to the body portion.

18. The adjustable implant of claim 17, wherein the hook portion includes a movable clamp member.

* * * * *